United States Patent
Epstein et al.

(10) Patent No.: US 11,786,551 B2
(45) Date of Patent: Oct. 17, 2023

(54) METHODS FOR TREATING HEART DISEASE VIA REDIRECTED T CELL IMMUNOTHERAPIES

(71) Applicant: THE TRUSTEES OF THE UNIVERSITY OF PENNSYLVANIA, Philadelphia, PA (US)

(72) Inventors: Jonathan Epstein, Radnor, PA (US); Haig Aghajanian, Lafayette Hill, PA (US); Steven M. Albelda, Philadelphia, PA (US); Ellen Puré, Bryn Mawr, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 137 days.

(21) Appl. No.: 16/651,144

(22) PCT Filed: Sep. 25, 2018

(86) PCT No.: PCT/US2018/052605
§ 371 (c)(1),
(2) Date: Mar. 26, 2020

(87) PCT Pub. No.: WO2019/067425
PCT Pub. Date: Apr. 4, 2019

(65) Prior Publication Data
US 2020/0268796 A1    Aug. 27, 2020

Related U.S. Application Data

(60) Provisional application No. 62/563,323, filed on Sep. 26, 2017.

(51) Int. Cl.
| | |
|---|---|
| *A61K 35/17* | (2015.01) |
| *A61P 9/04* | (2006.01) |
| *C07K 16/40* | (2006.01) |

(52) U.S. Cl.
CPC .............. *A61K 35/17* (2013.01); *A61P 9/04* (2018.01); *C07K 16/40* (2013.01)

(58) Field of Classification Search
None
See application file for complete search history.

(56) References Cited

U.S. PATENT DOCUMENTS

| | | |
|---|---|---|
| 9,365,641 B2 | 6/2016 | June et al. |
| 2004/0137513 A1 | 7/2004 | Devaux |
| 2007/0135998 A1 | 6/2007 | Van Vlijmen |
| 2011/0052606 A1 | 3/2011 | Spee |
| 2014/0099340 A1 | 4/2014 | June et al. |
| 2016/0060356 A1 | 3/2016 | Bacac |
| 2016/0176964 A1 | 6/2016 | Arathoon |
| 2016/0194402 A1 | 7/2016 | Van Eenennaam |
| 2016/0326265 A1 | 11/2016 | June |
| 2017/0081411 A1 | 3/2017 | Engels et al. |
| 2017/0226225 A1 | 8/2017 | Chen |
| 2018/0022822 A1 | 1/2018 | Brokopp |
| 2019/0167721 A1 | 6/2019 | Fan |
| 2019/0202902 A1 | 7/2019 | Chen |

FOREIGN PATENT DOCUMENTS

| | | |
|---|---|---|
| WO | 2000029584 | 5/2000 |
| WO | 2005011376 | 2/2005 |
| WO | 2011040972 | 4/2011 |
| WO | 2014/055442 A2 | 4/2014 |
| WO | 2014184194 | 11/2014 |
| WO | 2015032906 | 3/2015 |
| WO | 2015/090229 A1 | 6/2015 |
| WO | 2016070050 | 5/2016 |
| WO | 2017181119 | 10/2017 |
| WO | 2018105560 | 6/2018 |
| WO | 2018/148440 A1 | 8/2018 |
| WO | 2019126724 | 6/2019 |
| WO | 2019173291 | 9/2019 |
| WO | 2021061708 | 4/2021 |
| WO | 2021061778 | 4/2021 |
| WO | 2022081694 | 4/2022 |

OTHER PUBLICATIONS

Cartellier et al., 2010 J Biomed Biotechnol;2010:956304.*
Lo, A. et al., "Tumor-Promoting Desmoplasia Is Disrupted by Depleting FAP-Expressing Stromal Cells", Cancer Research, Jul. 2015, vol. 75, Issue 14, pp. 2800-2810.
Sun, S. et al., "Immunotherapy with CAR-Modified T Cells: Toxicities and Overcoming Strategies", Immunotherapy and Vaccine Development, Apr. 17, 2018, vol. 2018, Article ID 2386187, pp. 1-10.

(Continued)

*Primary Examiner* — Sharon X Wen
(74) *Attorney, Agent, or Firm* — Saul Ewing LLP; Kathryn Doyle

(57) ABSTRACT

The present invention includes compositions and methods for treating heart disease and/or heart failure. In one embodiment, the treatment includes administering to the subject a cell genetically modified to express a chimeric antigen receptor (CAR), comprising an antigen binding domain specific for fibroblast activation protein (FAP). In another embodiment, the treatment includes administering a cell genetically modified to express a T cell receptor (TCR) specific for an activated fibroblast.

11 Claims, 27 Drawing Sheets
Specification includes a Sequence Listing.

(56) References Cited

OTHER PUBLICATIONS

Wang, L-C. S. et al., "Targeting fibroblast activation protein in tumor stroma with chimeric antigen receptor T cells can inhibit tumor growth and augment host immunity without severe toxicity", Cancer Immunol Res, Feb. 2014, vol. 2, No. 2, pp. 154-166.

Kaur, H. et al., "Targeted Ablation of Periostin-Expressing Activated Fibroblasts Prevents Adverse Cardiac Remodeling in Mice", Circ Res, Jun. 10, 2016, vol. 118, No. 12, pp. 1906-1917.

Tillmanns, J. et al., "Fibroblast activation protein alpha expression identifies activated fibroblasts after myocardial infarction", Journal of Molecular and Cellular Cardiology, Oct. 2015, vol. 87, pp. 194-203.

International Search Report and Written Opinion dated Mar. 4, 2019, of counterpart International Application No. PCT/US18/56205.

Petrausch, Ulf et al., "Re-directed T cells for the treatment of fibroblast activation protein (FAP)-positive malignant pleural mesothelioma (FAPME-1)," BMC Cancer, 12:615, pp. 1-7 (Dec. 22, 2012).

Shah, Ami et al., "Heart Failure: A Class Review of Pharmacotherapy," P&T, vol. 42, No. 7, pp. 464-472 (Jul. 1, 2017).

Geyer, Mark B. et al.: "Review: Current clinical applications of chimeric antigen receptor (CAR) modified T cells," Cytotherapy, vol. 18, No. 11, pp. 1393-1409 (Nov. 2016).

Aghajanian, Haig et al., "Targeting cardiac fibrosis with engineered T cells," Nature, vol. 573, No. 7774, pp. 430-433 (Sep. 2019).

Extended European Search Report, dated of completion Dec. 13, 2021, for European Application No. 18861807.8.

International Search Report for PCT/US20/52227 (dated Jan. 27, 2021).

International Search Report for PCT/US20/52121 (dated Feb. 10, 2021).

Roberts, E. W., et al., "Depletion of stromal cells expressing fibroblast activation protein-[alpha] from skeletal muscle and bone marrow results in cachexia and anemia," J. Exp. Med., vol. 210, No. 6 :1137-1151 (2013).

* cited by examiner

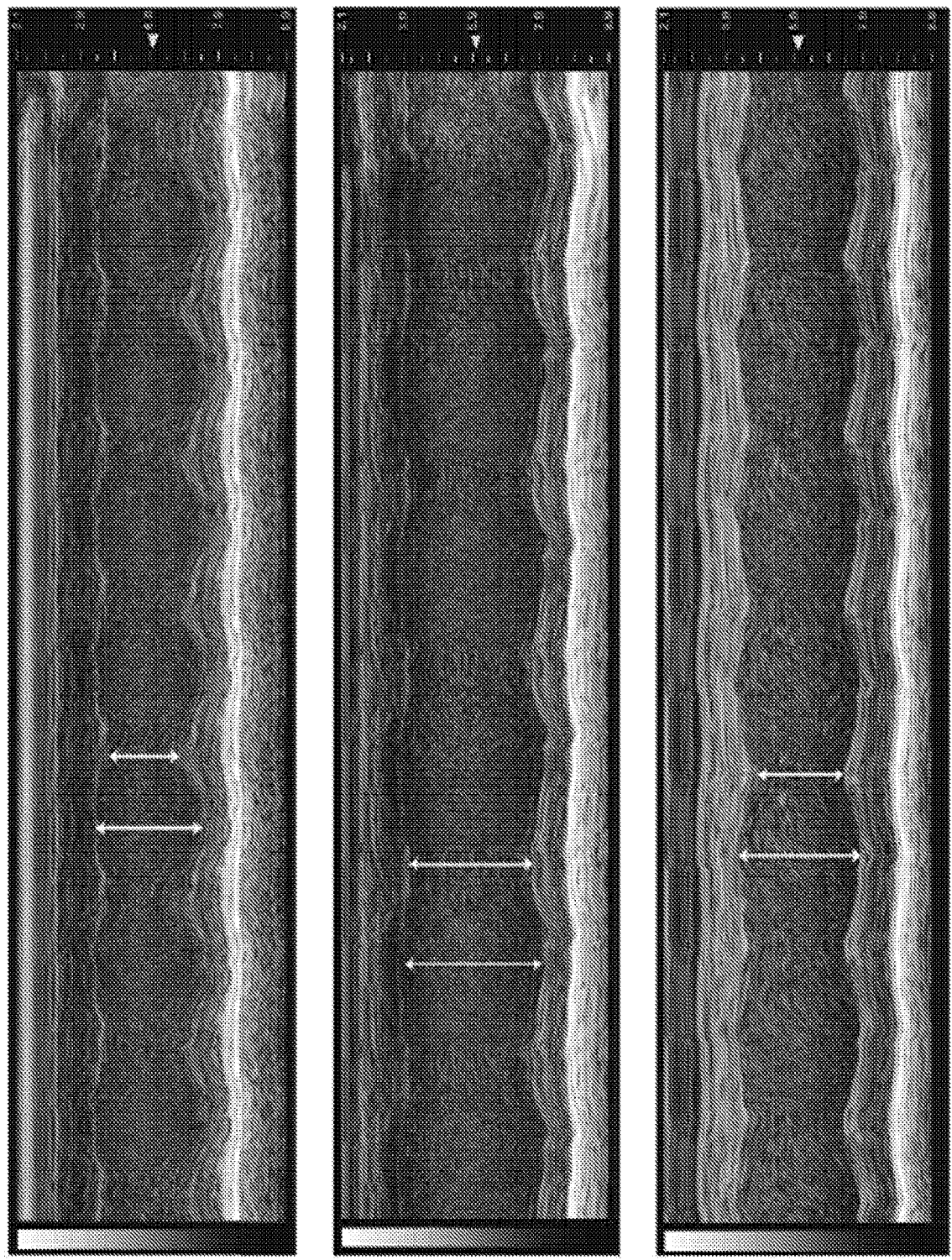

| SYMBOL | HCM | | DCM | |
| --- | --- | --- | --- | --- |
| | Fold Change | P Value | Fold Change | P Value |
| FAP | 3.92 | 6.97E-28 | 3.11 | 3.12E-36 |
| THY1 | 3.92 | 6.40E-20 | 3.12 | 5.07E-27 |
| POSTN | 2.64 | 1.40E-11 | 2.02 | 3.73E-13 |
| COL1A1 | 2.22 | 1.83E-15 | 2.71 | 1.04E-41 |
| WT1 | 1.74 | 6.29E-12 | 1.57 | 4.17E-16 |
| COL3A1 | 1.53 | 1.28E-05 | 1.77 | 8.72E-18 |
| TCF21 | 1.39 | 1.01E-05 | 1.59 | 5.26E-19 |
| VIM | 1.26 | 1.43E-12 | 1.20 | 1.60E-16 |
| ACTA2 | 1.26 | 2.64E-03 | 1.22 | 7.16E-05 |
| DDR2 | 1.05 | 0.21 | 1.02 | 0.47 |
| S100A4 | -1.00 | 0.96 | -1.03 | 0.33 |
| FN1 | -1.01 | 0.90 | 1.11 | 0.06 |
| P4HA1 | -1.18 | 4.11E-04 | -1.11 | 1.10E-03 |
| PDGFRA | -1.25 | 1.40E-05 | -1.17 | 9.98E-06 |

FIG. 10

METHODS FOR TREATING HEART DISEASE VIA REDIRECTED T CELL IMMUNOTHERAPIES

CROSS-REFERENCE TO RELATED APPLICATIONS

The present application is a 35 U.S.C. § 371 national phase application from, and claims priority to, International Application No. PCT/US2018/052605 filed Sep. 25, 2018, and published under PCT Article 21(2) in English, and is entitled to priority under 35 U.S.C. § 119(e) to U.S. Provisional Application No. 62/563,323 filed Sep. 26, 2017, all of which are incorporated herein by reference in their entireties.

STATEMENT REGARDING FEDERALLY SPONSORED RESEARCH OR DEVELOPMENT

This invention was made with government support under HL140018 and HL784321 awarded by the National Institutes of Health. The government has certain rights in the invention.

SUMMARY OF THE INVENTION

As described herein, the present invention relates to compositions and methods for treating heart disease and/or heart failure via redirected T cell immunotherapy (e.g. CAR T cell therapy and engineered TCR therapy).

One aspect of the invention includes a method for treating heart disease and/or heart failure in a subject in need thereof. The method comprises administering to the subject a cell genetically modified to express a chimeric antigen receptor (CAR). The CAR comprises an antigen binding domain specific for fibroblast activation protein (FAP).

Another aspect of the invention includes a method for treating heart disease and/or heart failure in a subject in need thereof. The method comprises administering to the subject a cell genetically modified to express a T Cell Receptor (TCR) specific for an activated fibroblast.

In various embodiments of the above aspects or any other aspect of the invention delineated herein, the heart disease is selected from the group consisting of cardiac fibrosis, hypertensive heart disease, diastolic dysfunction, heart failure with preserved ejection fraction, myocardial infarction, ischemic cardiomyopathy, hypertrophic cardiomyopathy, arrhythmia, atrial fibrillation, arrhythmogenic right ventricular dysplasia, dilated cardiomyopathy, an inherited form of heart disease, muscular dystrophy, infective cardiomyopathy, transplant cardiomyopathy, radiation induced cardiac fibrosis, an autoimmune related heart condition, sarcoid cardiomyopathy, lupus, a toxin related heart condition, a drug related heart condition, amyloidosis, diabetic cardiomyopathy, reactive interstitial fibrosis, replacement fibrosis, infiltrative interstitial fibrosis, and endomyocardial fibrosis In one embodiment, the cell is a T cell.

In one embodiment, the administering comprises adoptive cell transfer.

In one embodiment, the CAR comprises a nucleic acid sequence comprising SEQ ID NO: 1. In one embodiment, the CAR comprises an amino acid sequence encoded by a nucleic acid sequence comprising SEQ ID NO: 1. In one embodiment, the antigen binding domain comprises a nucleic acid sequence comprising SEQ ID NO: 2. In one embodiment, the antigen binding domain comprises an amino acid sequence encoded by a nucleic acid sequence comprising SEQ ID NO: 2.

In one embodiment, the CAR is a switchable CAR. In one embodiment, a second agent is administered to the subject to activate the switchable CAR.

BACKGROUND OF THE INVENTION

Heart disease or cardiovascular disease generally refers to conditions that involve narrowed or blocked blood vessels that can lead to a heart attack, chest pain (angina) or stroke. Other heart conditions, such as those that affect the heart's muscle, valves or rhythm, also are considered forms of heart disease. Fibroblasts comprise the largest cell population in the myocardium. In heart disease, the number of fibroblasts is increased either by replication of the resident myocardial fibroblasts, migration and transformation of circulating bone marrow cells, or by transformation of endothelial/epithelial/epicardial cells into fibroblasts and myofibroblasts. The primary function of fibroblasts is to produce structural proteins that comprise the extracellular matrix (ECM). This can be a constructive process; however, hyperactivity of cardiac fibroblasts can result in excess production and deposition of ECM proteins in the myocardium, known as fibrosis, with adverse effects on cardiac structure and function. Cardiac fibrosis may refer to an abnormal thickening of the heart valves due to inappropriate proliferation of cardiac fibroblasts, but more commonly refers to the excess deposition of extracellular matrix in the cardiac muscle. There are currently no therapies available to treat or reverse cardiac fibrosis. Cardiac fibrosis can also contribute to pathology in some forms of genetic cardiac diseases including muscular dystrophies.

Heart failure remains a leading cause of death worldwide and the most common hospital discharge diagnosis in the United States. Nearly all forms of heart failure are associated with cardiac fibrosis, including those with reduced ejection fraction or preserved ejection fraction (heart failure with preserved ejection fraction, HFpEF). Myocardial fibrosis and associated poor diastolic relaxation are thought to be the central drivers of symptoms in patients with HFpEF. Many forms of cardiomyopathy not associated with coronary artery disease also display excessive fibrosis, including ischemic cardiomyopathy, sarcoid cardiomyopathy, hypertrophic cardiomyopathy, hypertensive heart disease, and inherited forms of muscular dystrophy and dilated cardiomyopathy. Although quiescent fibroblasts are an important component of the normal structure of the myocardium, activated, pathological fibroblasts induced by injury or disease negatively impact compliance and stiffness and signal to cardiac myocytes to further negatively impact function. Nevertheless, no therapies are known to directly target excessive fibrosis. Very few interventions have been shown to improve cardiac function and clinical outcomes in patients with HFpEF despite the enormous burden of disease across the population. Although genetic expression of cytotoxic agents in activated cardiac fibroblasts has been shown to reduce fibrosis and improve function in mouse models of hypertension or ischemia, this approach is not directly translatable to humans.

A need exists for novel compositions and methods to treat heart diseases, including cardiac fibrosis. The present invention satisfies this need.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIGS. 1A-1F illustrate the finding that FAP-CAR T cells can reverse cardiac fibrosis. FIG. 1A shows Masson's trichrome stain for fibrosis (left, center) and immunohistochemistry for Fap (right) in adjacent WT coronal heart sections 1 week after continuous saline (top) or angiotensin II/phenylephrine (bottom) treatment. (inset; left ventricle). FIG. 1B is a schematic diagram of experiments for FAP-CAR T cell ablation of cardiac fibroblast. C57BL/6 mice were continuously administered angiotensin II and phenylephrine via osmotic pump to induce cardiac injury and fibrosis. FAP-CAR T cells were adoptively transferred 1 and 2 weeks after pump implantation. Mice were evaluated and sacrificed at 4 weeks to assess for fibrosis. FIG. 1C shows Picro-Sirius Red staining of heart coronal sections in mice treated with saline (left), angiotensin II/phenylephrine (center), or angiotensin II/phenylephrine+FAP-CAR T cells (right) to evaluate fibrosis. Magnification of left ventricular fibrosis is shown on the bottom. FIG. 1D shows quantification of cardiac fibrosis. ***$P<0.001$, *$P<0.05$, ns=not significant (one way ANOVA between groups $P<0.001$; post-hoc multiple comparisons, Tukey's test, $n \geq 7$). FIG. 1E shows a comparison of cardiac functional parameters and body weight between experimental and control groups. ***$P<0.001$,*$P<0.05$, ns=not significant (one-way ANOVA between groups; posthoc multiple comparisons on significant ($P<0.05$) ANOVA, Tukey's test, $n \geq 7$). FIG. 1F shows M mode echocardiography of mice treated with saline (top), angiotensin II/phenylephrine (center), or angiotensin II/phenylephrine+FAP-CAR T cells (bottom), (arrows; systole, diastole). Scale bars=100 μm.

FIG. 6A shows results from FS=Fractional shortening; HR=heart rate; BW=body weight; LVAEpid=Left ventricular epicardial area (diastole); LVAENDd=Left ventricular endocardial area (diastole); and LVAENDs=Left ventricular endocardial area (systole). FIG. 6B shows results from LVLd=Left ventricular endocardial length (diastole); LVLs=Left ventricular endocardial length (systole); EDV=End diastolic volume; ESV=End systolic volume; SV=Stroke volume; and CO=Cardiac output. FIG. 6C shows results from IVSd=Interventricular septal end diastole; IVSs=Interventricular septal end systole; LVIDd=Left ventricular internal diameter end diastole; LVIDs=Left ventricular internal diameter end systole; MV E=Early ventricular filling velocity; and E/E'=ratio of mitral peak velocity of early filling (E) to early diastolic mitral annular velocity (F).

FIG. 7A shows Masson's trichrome stain (left, center) and FAP immunohistochemistry (right) on adjacent heart coronal sections 1 week after commencement of continuous AngII/PE treatment. FAP expression was present in interstitial, but not perivascular fibroblast (white arrowheads). FIG. 7B shows Picro-Sirius Red staining for perivascular fibrosis (black arrowheads) on heart coronal sections from mice treated for 4 weeks with either saline, AngII/PE, or AngII/PE+FAP-CAR T cells. Scale bars=100 μm.

FIG. 9A is a heat map of cardiac fibroblast gene expression changes (fold change) in patients with hypertrophic cardiomyopathy (HCM) and dilated cardiomyopathy (DCM) when compared with non-failing hearts (NF). FIG. 9B shows fibroblast activation protein (FAP) expression in NF, HCM, and DCM myocardium. Each data point represents an individual patient (n=122 (NF), 27 (HCM), 89 (DCM)). FIG. 9C shows immunohistochemistry for FAP expression in left ventricular free-wall sections from 6 individual NF (#1,2), HCM (#3,4), and DCM (#5,6) human samples. Scale bars=100 μm.

FIG. 10 is a table illustrating fold change and P values of cardiac fibroblast specific gene expression from patients with hypertrophic cardiomyopathy (HCM) and dilated cardiomyopathy (DCM) as compared with non-failing hearts.

FIG. 11A is a schematic representation of cardiac injury and T cell mediated cardiac fibroblast ablation. Mice were continuously administered angiotensin II and phenylephrine via osmotic pump to induce cardiac injury and fibrosis, and injected with tamoxifen to trigger Cre-mediated OVA expression in the CFs. CD8+ OT-I T cells were adoptively transferred 1 week after pump implantation and mice were sacrificed 4 weeks post-implantation for analysis. FIG. 11B shows Picro-Sirius Red staining of heart coronal sections to evaluate the level of fibrosis. Higher magnification of left ventricular fibrosis is shown on the bottom panel. FIG. 11C shows quantification of ventricular fibrosis. ***$P<0.001$, *$P<0.05$, ns=not significant (one-way ANOVA between groups $P<0.001$; post-hoc multiple comparisons, Tukey's test, $n \geq 7$). Scale bars=100 μm.

FIG. 13A shows control and experimental hearts were measured (weight, mg) and images captured. FIG. 13B shows quantification of heart weight to body weight (HW/BW) ratio of various genotypes and conditions. ***$P<0.001$ (one-way ANOVA between groups $P<0.001$; post-hoc multiple comparisons, Tukey's test, $n \geq 7$).

DETAILED DESCRIPTION

Definitions

Figure 1A:
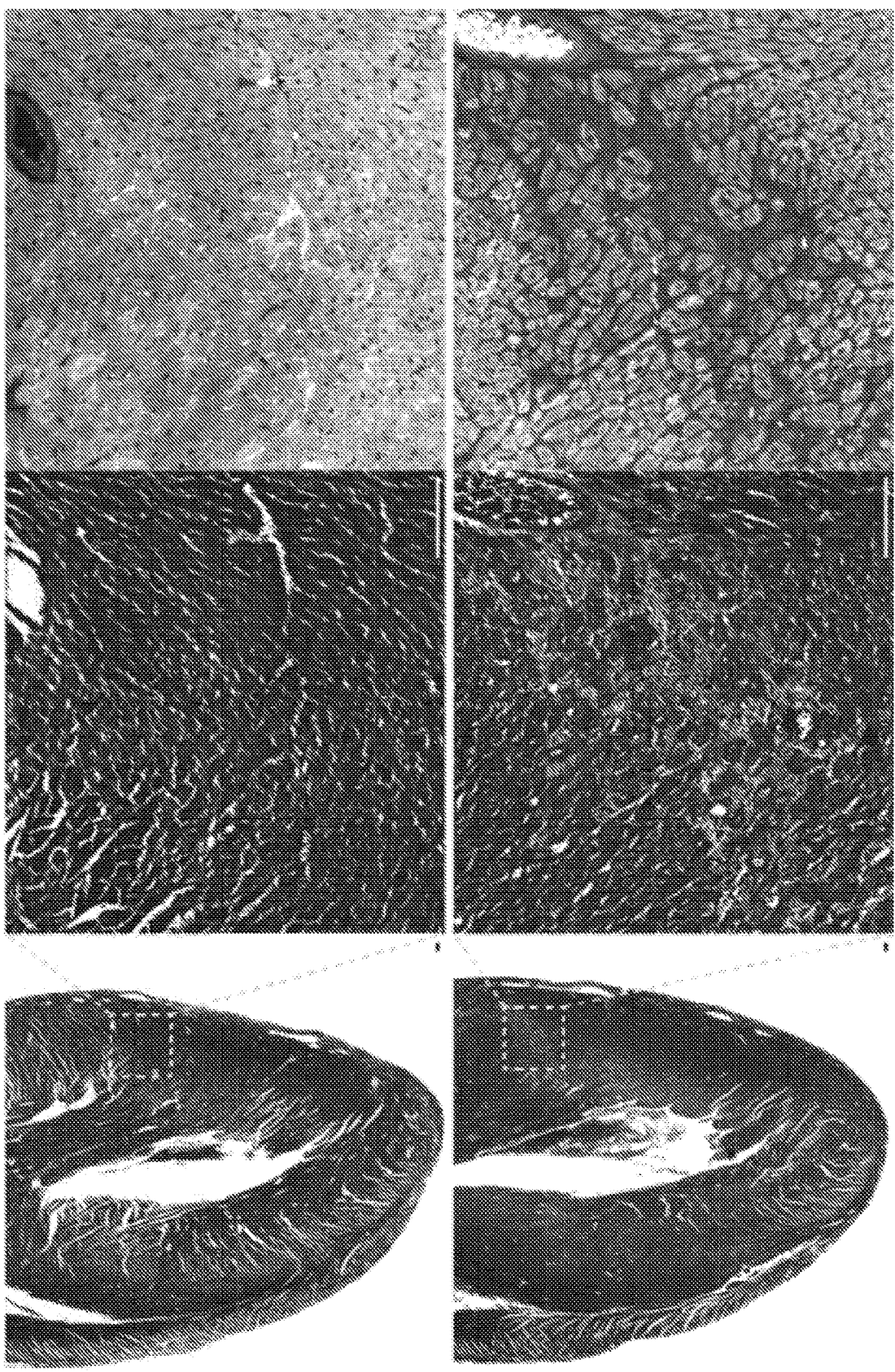

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. α and β light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

"Allogeneic" refers to any material derived from a different animal of the same species.

"Xenogeneic" refers to any material derived from an animal of a different species.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs has specificity to a selected target, for example a B cell surface receptor. CARs may also comprise an intracellular activation domain, a transmembrane domain and an extracellular domain comprising a tumor associated antigen binding region. In some aspects, CARs comprise an extracellular domain comprising an anti-B cell binding domain fused to CD3-zeta transmembrane and intracellular domain.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

As used herein, 'FAP" refers to fibroblast activation protein. The term should be construed to include not only fibroblast activation protein, but variants, homologs, fragments and portions thereof to the extent that such variants, homologs, fragments and portions thereof retain the activity of FAP as disclosed herein.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

When "an immunologically effective amount," "an autoimmune disease-inhibiting effective amount," or "therapeutic amount" is indicated, the precise amount of the compositions of the present invention to be administered can be determined by a physician or researcher with consideration of individual differences in age, weight, tumor size, extent of infection or metastasis, and condition of the patient (subject).

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

By the term "modified" as used herein, is meant a changed state or structure of a molecule or cell of the invention. Molecules may be modified in many ways, including chemically, structurally, and functionally. Cells may be modified through the introduction of nucleic acids.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an WIC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic cell, a memory T cell, regulatory cell, natural killer T cell, and gamma delta T cell.

The term "therapeutic" as used herein means a treatment and/or prophylaxis. A therapeutic effect is obtained by suppression, remission, or eradication of a disease state. The term "therapeutically effective amount" refers to the amount of the subject compound that will elicit the biological or medical response of a tissue, system, or subject that is being sought by the researcher, veterinarian, medical doctor or other clinician.

The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides compositions and methods useful for treating heart disease and/or heart failure via redirected T cell immunotherapy (e.g. CAR T cell therapy and engineered TCR therapy). The invention provides therapy for treating patients with heart failure or heart conditions due to many causes, including but not limited to hypertensive heart disease, diastolic dysfunction, heart failure with preserved ejection fraction, myocardial infarction, and/or stiffness of the heart due to fibrosis, including cardiac fibrosis that can accompany genetic disorders such as muscular dystrophy, renal disease, cardiac transplant rejection and other cardiac conditions.

In certain embodiments, the invention provides therapy for treatment or reversal of cardiac fibrosis. The invention involves, in one embodiment, using chimeric antigen receptor T cells (CAR T cells) specific for an activated cardiac fibroblast protein (fibroblast activation protein—FAP) to reduce pathological cardiac fibrosis and improve cardiac function. In another embodiment, the invention includes use of a genetically modified cell comprising a T cell receptor (TCR) that specifically targets an activated fibroblast (i.e. FAP, Periostin).

Methods of Treatment

In one aspect, the invention includes a method for treating heart disease and/or heart failure in a subject in need thereof. In one embodiment, the method comprises administering to the subject a cell genetically modified to express a chimeric antigen receptor (CAR). The CAR comprises an antigen binding domain specific for fibroblast activation protein (FAP). In one embodiment, the method comprises administering to the subject a cell genetically modified to express a T Cell Receptor (TCR) specific for an activated fibroblast. In one embodiment, the TCR is specific for Periostin expressing cells.

The types of heart diseases to be treated include but are not limited to cardiac fibrosis, hypertensive heart disease, diastolic dysfunction, heart failure with preserved ejection fraction, myocardial infarction, ischemic cardiomyopathy, hypertrophic cardiomyopathy, arrhythmias including atrial fibrillation, arrhythmogenic right ventricular dysplasia, dilated cardiomyopathy (including idiopathic and familial forms), hypertensive heart disease, inherited forms including muscular dystrophy, infective cardiomyopathy (e.g. Chagas disease, rheumatic fever), transplant cardiomyopathy, radiation induced cardiac fibrosis, autoimmune (Sarcoid cardiomyopathy, lupus), toxin or drug related, amyloidosis, diabetic cardiomyopathy, and other types of cardiac fibrosis including but not limited to reactive interstitial fibrosis, replacement fibrosis, infiltrative interstitial fibrosis, and endomyocardial fibrosis.

In one embodiment, the CAR used to treat heart disease or heart failure comprises a nucleic acid sequence comprising SEQ ID NO: 1. In one embodiment, the CAR comprises an amino acid sequence encoded by a nucleic acid sequence comprising SEQ ID NO: 1. In one embodiment, the antigen binding domain comprises a nucleic acid sequence comprising SEQ ID NO: 2. In one embodiment, the antigen binding domain comprises an amino acid sequence encoded by a nucleic acid sequence comprising SEQ ID NO: 2.

In one embodiment, the cell genetically modified to express a CAR is a T cell. The cell or population of T cells can be adoptively transferred into the subject using methods and protocols known to one of ordinary skill in the art.

Administration of the compositions of the invention (e.g. the modified/redirected cells) to a human patient can be by any route, including but not limited to intravenous, intradermal, transdermal, subcutaneous, intramuscular, inhalation (e.g., via an aerosol), buccal (e.g., sub-lingual), topical (i.e., both skin and mucosal surfaces, including airway surfaces), intrathecal, intraarticular, intraplural, intracerebral, intraarterial, intraperitoneal, oral, intralymphatic, intranasal, rectal or vaginal administration, by perfusion through a regional catheter, or by direct intralesional injection. In one embodiment, the compositions of the invention (e.g. the modified/redirected cells) are administered by intravenous push or intravenous infusion given over defined period (e.g., 0.5 to 2 hours). In one embodiment, the compositions of the invention are adoptively transferred. The compositions of the invention can be delivered by peristaltic means or in the form of a depot, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered. In particular embodiments, the route of administration is via bolus or continuous infusion over a period of time, once or twice a week. In other particular embodiments, the route of administration is by subcutaneous injection given in one or more sites (e.g. thigh, waist, buttocks, arm), optionally once or twice weekly. In one embodiment, the compositions, and/or methods of the invention are administered on an outpatient basis.

In certain embodiments, the modified cell (e.g. FAP-CAR T cell or cell modified to express a TCR specific for an activated fibroblast) or population of cells are administered in such a way as to focus their delivery to the heart. For example, the cell or population of cells can be injected intravenously into the coronary arteries. In certain embodiments a cardiac catheter can be used to deliver the cell or population of cells. In certain embodiments, a focused delivery of the cell or population of cells to the myocardium is administered.

The modified cell (e.g. FAP-CAR T cell or cell modified to express a TCR specific for an activated fibroblast) or population of cells can be administered to a subject alone or in combination with a second agent. In certain embodiments, a FAP-CAR T cell is administered in its 'active' form. In other embodiments, the FAP-CAR T cell is administered in an 'inactive' form, and a second agent is administered that 'activates' the FAP-CAR T cell. The second agent can include, but is not limited to a small molecule, an antibody, an engineered virus, an engineered cell, a laser light, electromagnetic radiation, and a nanoparticle. In one non-limiting example, a T cell comprising a FAP-CAR with a switch receptor can be administered to a subject, then a second agent is administered that turns on the switch receptor, activating the FAP-CAR.

Those skilled in the art will appreciate that dosages can be selected based on a number of factors including the age, sex, species and condition of the subject (e.g., activity of disease or disorder), and/or the disease to be treated, and can be determined by one of skill in the art. For example, effective amounts of the compositions of the invention may be extrapolated from dose-response curves derived from in vitro test systems or from animal model (e.g. the cotton rat or monkey) test systems. Models and methods for evaluation of the effects of antibodies are known in the art (Wooldridge et al., Blood, 89(8): 2994-2998 (1997), incorporated by reference herein in its entirety). In certain embodiments, for a particular disease or disorder, therapeutic regimens standard in the art for antibody therapy can be used with the compositions and methods of the invention.

Examples of dosing regimens that can be used in the methods of the invention include, but are not limited to, daily, three times weekly (intermittent), weekly, or every 14 days. In certain embodiments, dosing regimens include, but are not limited to, monthly dosing or dosing every 6-8 weeks. Those skilled in the art will appreciate that dosages are generally higher and/or frequency of administration greater for initial treatment as compared with maintenance regimens.

Chimeric Antigen Receptors (CARs)

In one embodiment, the present invention relates to a chimeric antigen receptor (CAR). The CAR comprises an extracellular domain, a transmembrane domain, and an intracellular domain. The extracellular domain comprises a target-specific binding element otherwise referred to as an antigen binding domain. In some embodiments, the extracellular domain also comprises a hinge domain. In certain embodiments, the intracellular domain or otherwise the cytoplasmic domain comprises, a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

The extracellular domain, transmembrane domain, and intracellular domain can be derived from any desired source of such domains. In one embodiment, the CAR comprises a nucleic acid sequence comprising SEQ ID NO: 1. In one embodiment, the CAR comprises an amino acid sequence encoded by a nucleic acid sequence comprising SEQ ID NO: 1.

mFAP-CAR (SEQ ID NO: 1)

```
atggccctgcctgtgacagccctgctgctgcctctggctctgctgctgca
tgccgctagacctggatcccaggtgcagctgaaagagtccggcggaggac
tggtgcagcctggcggatctctgaagctgagctgtgctgccagcggcttc
accttcagcagctacggcatgagctgggtgcgacagaccgccgacaagag
actggaactggtggctaccaccaacaacggcggcgtgacctactacc
ccgacagcgtgaagggcagattcaccatctccagagacaacgccaagaac
accctgtacctgcagatgagcagcctgcagagcgaggacaccgccatgta
ctactgcgccagatacggctactacgccatggattactggggccagggca
tcagcgtgaccgtgtctagcggaggcggcggatctggcggaggggatct
agtggcggaggctctgacgtgctgatgacccagacacctctgagcctgcc
agtgtccctgggcgaccaggccagcatcagctgtagaagcagccagagca
tcgtgcacagcaacggcaacacctacctggaatggtatctgcagaagccc
ggccagagcccaagctgctgatctacaaggtgtccaacagattcagcgg
cgtgcccgacagattctccggcagcggctctggcaccgacttcaccgtga
agatctccagggtggaagccgaggacctgggcgtgtactactgttttcaa
ggcagccacgtgccctacaccttcggcggaggcaccaagctggaaatcaa
ggctagctccggaaccacgacgccagcgccgcgaccaccaacaccggcgc
ccaccatcgcgtcgcagccctgtcctgcgcccagaggcgtgccggcca
gcggcggggggcgcagtgcacacgaggggctggacttcgcctgtgatat
ctacatctgggcgccttggccgggacttgtggggtccttctcctgtcac
tggttatcacccttactgcaaacggggcagaagaaactcctgtatata
ttcaaacaaccatttatgagaccagtacaaactactcaagaggaagatgg
ctgtagagccgatttccagaagaagaagaaggaggatgtgaactgagagt
gaagttcagcaggagcgcagacgccccgcgtacaagcagggccagaacc
agctctataacgagctcaatctaggacgaagagaggagtacgatgttttg
gacaagagacgtggccgggaccctgagatgggggggaaagccgagaaggaa
gaaccctcaggaaggcctgtacaatgaactgcagaaagataagatggcgg
aggcctacagtgagattgggatgaaaggcgagcgccggaggggcaagggg
cacgatggcctttaccagggtctcagtacagccaccaaggacacctacga
cgccttcacatgcaggccctgccccctcgc
```

Antigen Binding Domain

The antigen binding domain may be obtained from any of the wide variety of extracellular domains or secreted proteins associated with ligand binding and/or signal transduction. In one embodiment, the antigen binding domain may consist of an Ig heavy chain which may in turn be covalently associated with Ig light chain by virtue of the presence of CH1 and hinge regions, or may become covalently associated with other Ig heavy/light chain complexes by virtue of the presence of hinge, CH2 and CH3 domains. In the latter case, the heavy/light chain complex that becomes joined to the chimeric construct may constitute an antibody with a specificity distinct from the antibody specificity of the chimeric construct. Depending on the function of the antibody, the desired structure and the signal transduction, the entire chain may be used or a truncated chain may be used, where all or a part of the CH1, CH2, or CH3 domains may be removed or all or a part of the hinge region may be removed.

The present invention comprises an antigen binding domain that binds to fibroblast activation protein (FAP). As discussed elsewhere herein, the present invention provides that targeting an activated cardiac fibroblast which expresses FAP allows for the reduction and/or elimination of pathological cardiac fibrosis and improvement of cardiac function. In one embodiment, the antigen binding domain comprises a domain directed to FAP. FAP is expressed on a vast majority of stromal cells. In one embodiment, the CAR may be one for which a specific monoclonal antibody currently exists or can be generated in the future.

The CAR of the invention can be engineered to include any anti-FAP moiety that is specific to FAP. The antigen binding domain can be any domain that binds to the antigen including but not limited to monoclonal antibodies, polyclonal antibodies, synthetic antibodies, scFvs, human antibodies, humanized antibodies, and fragments thereof. In one embodiment, the antigen binding domain comprises a nucleic acid sequence comprising SEQ ID NO: 2. In one embodiment, the antigen binding domain comprises an amino acid sequence encoded by a nucleic acid sequence comprising SEQ ID NO: 2.

Anti-mFAP scFv (SEQ ID NO: 2)

```
caggtgcagctgaaagagtccggcggaggactggtgcagcctggcggatc
tctgaagctgagctgtgctgccagcggcttcaccttcagcagctacggca
tgagctgggtgcgacagaccgccgacaagagactggaactggtggctacc
accaacaacggcggcgtgacctactaccccgacagcgtgaagggcag
attcaccatctccagagacaacgccaagaacaccctgtacctgcagatga
gcagcctgcagagcgaggacaccgccatgtactactgcgccagatacggc
tactacgccatggattactggggccagggcatcagcgtgaccgtgtctag
cggaggcggcggatctggcggaggggatctagtggcggaggctctgacg
tgctgatgacccagacacctctgagcctgccagtgtccctgggcgaccag
gccagcatcagctgtagaagcagccagagcatcgtgcacagcaacggcaa
cacctacctggaatggtatctgcagaagcccggccagagccccaagctgc
tgatctacaaggtgtccaacagattcagcggcgtgcccgacagattctcc
ggcagcggctctggcaccgacttcaccgtgaagatctccagggtggaagc
cgaggacctgggcgtgtactactgttttcaaggcagccacgtgccctaca
ccttcggcggaggcaccaagctggaaatcaag
```

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker. In one embodiment, the transmembrane domain comprises a nucleic acid sequence comprising SEQ ID NO: 3. In one embodiment, the transmembrane domain comprises an amino acid sequence encoded by a nucleic acid sequence comprising SEQ ID NO: 3.

```
CD8a transmembrane domain
                                        (SEQ ID NO: 3)
atctacatctgggcgcccttggccgggacttgtggggtccttctcctgtc actggttatcacccttactgc
```

Intracellular Domain

The cytoplasmic domain or otherwise the intracellular domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular domain can be employed, in many cases it is not necessary to use the entire chain. To the extent that a truncated portion of the intracellular domain is used, such truncated portion may be used in place of the intact chain as long as it transduces the effector function signal. The term intracellular domain is thus meant to include any truncated portion of the intracellular domain sufficient to transduce the effector function signal.

Preferred examples of intracellular domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of intracellular signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary intracellular signaling sequences regulate primary activation of the TCR complex either in a stimulatory way, or in an inhibitory way. Primary intracellular signaling sequences that act in a stimulatory manner may contain signaling motifs which are known as immunoreceptor tyrosine-based activation motifs or ITAMs.

Examples of ITAM containing primary intracellular signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that intracellular signaling molecule in the CAR of the invention comprises an intracellular signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR of the invention. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with 4-1BB as the co-stimulatory signaling element, other costimulatory elements are within the scope of the invention.

The intracellular signaling sequences within the intracellular domain of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In yet another embodiment, the intracellular domain is designed to comprise the signaling domain of CD3-zeta and the signaling domain of 4-1BB.

In one embodiment, the intracellular domain comprises a nucleic acid sequence comprising SEQ ID NO: 4. In one embodiment, the intracellular domain comprises a nucleic acid sequence comprising SEQ ID NO: 5. In one embodiment, the intracellular domain comprises a nucleic acid sequence comprising SEQ ID NO: 4 and SEQ ID NO: 5.

In one embodiment, the intracellular domain comprises an amino acid sequence encoded by a nucleic acid sequence comprising SEQ ID NO: 4. In one embodiment, the intracellular domain comprises an amino acid sequence encoded by a nucleic acid sequence comprising SEQ ID NO: 5. In one embodiment, the intracellular domain comprises an amino acid sequence encoded by a nucleic acid sequence comprising SEQ ID NO: 4 and SEQ ID NO: 5.

```
4-1BB intracellular domain
                                        (SEQ ID NO: 4)
aaacggggcagaaagaaactcctgtatatattcaaacaaccatttatgag accagtacaaactactcaagaggaagatggctgtagctgccgatttccag aagaagaagaaggaggatgtgaactg
```

-continued

CD3-zeta signaling domain (SEQ ID NO: 5)
Agagtgaagttcagcaggagcgcagacgccccgcgtacaagcagggcca gaaccagctctataacgagctcaatctaggacgaagagaggagtacgatg ttttggacaagagacgtggccgggaccctgagatgggggaaagccgaga aggaagaaccctcaggaaggcctgtacaatgaactgcagaaagataagat ggcggaggcctacagtgagattgggatgaaaggcgagcgccggaggggca aggggcacgatggcctttaccagggtctcagtacagccaccaaggacacc tacgacgcccttcacatgcaggccctgccccctcgc Strategies for Overcoming CAR Toxicities Certain embodiments of the invention include compositions and methods for overcoming toxicity of CAR T cell based therapy. For example, the durability of CAR T cells in the body after completion of the therapeutic aspects can potentially lead to undesired side effects, including but not limited to off-target toxicity, on-target toxicity, and neurotoxicity (Sun et al. (2018) *J Immunol Res*, Article ID2386187). The compositions and methods described herein can further comprise strategies to overcome these risks. For example, in certain embodiments, the CAR of the present invention can further comprise a suicide gene, e.g an HSV-tk suicide gene (Bordingnon et al. (1995) *Human Gene Therapy*, vol. 6, no. 6, pp 813-819). The HSV-tk gene can be co-expressed in the T cell, and upon expression it turns the non-toxic prodrug GCV into GCV-triphosphate, leading to cell death by halting DNA replication. In certain embodiments, the T cell can co-express iCasp9. iCasp9 binds to the small molecule AP1903 and results in dimerization, which activates the intrinsic apoptotic pathway. In certain embodiments, a targetable surface antigen is co-expressed in the T cell (e.g. CD20 and truncated EGFR), wherein the modified cell can be eliminated through complement/antibody-dependent cellular cytotoxicity (CDC/ADCC) by administering the associated monoclonal antibody.

In certain embodiments, the CAR comprises targeted activation, e.g. wherein T cell activation is controlled through combinatorial antigen-targeting activation with separated signals. In one non-limiting embodiment, the invention can comprise a dual-targeting CAR strategy, wherein the CAR of the present invention, which is specific for a first antigen (e.g. FAP) is utilized along with a second CAR that is specific for a (different) second antigen. This dual CAR strategy is used to ensure that activation occurs only on the cells that display both antigens. In another embodiment, the CAR of the invention is a Tan-CAR, which has specificity for two antigens via the expression of two tandemly arranged scFvs coupled to the same signaling domain. In certain embodiments, the cells of invention can include an inhibitory receptor (iCAR) comprising, for example, an intracellular domain of PD-1 or CTLA-4, which can be triggered by an antigen expressed on normal cells. This results in inhibition of CART cell function via a self-regulating switch that allows targeting of cells/tissue expressing a specific antigen (e.g. FAP) while normal cells/tissue are spared.

In certain embodiments, the CAR is a switchable CAR or regulatable CAR. For example, the CAR can include an On-switch, a synNotch AND-gate circuit, or an antibody-based switch. In certain embodiments, a recombinant antibody is used as a switch (e.g. TAA-specific monoclonal antibody, chemically or enzymatically modified antibody-hapten conjugates). In certain embodiments, an antibody or fragment thereof targeting FAP is modified to be recognized by a CAR engineered to recognize an epitope conjugated to an FAP antibody or fragment thereof. For example, a peptide neo-epitope (PNE) can be conjugated to an antigen-specific antibody or fragment thereof (e.g. anti-FAP antibody or Fab). Since PNE is not an endogenous antigen, the activation of the CAR-T cell is dependent on the presence of the switch. Examples of switchable or regulatable CARs can be found for example in International Application Publication numbers WO 2015/090229 A1 and WO 2018/148440 A1, and Sun et al. (2018) *J Immunol Res*, Article ID2386187. While certain switchable CARs and regulatable CARs are exemplified herein, the invention should be construed to include any switchable CAR or regulatable CAR known in the art.

Sources of T Cells

In certain embodiments, prior to expansion, a source of T cells is obtained from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

Expansion of T Cells

In certain embodiments, the T cells disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more by culturing the electroporated population.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

Pharmaceutical Compositions

Pharmaceutical compositions of the present invention may comprise the modified T cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The cells of the invention to be administered may be autologous, allogeneic or xenogeneic with respect to the subject undergoing therapy.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It can generally be stated that a pharmaceutical composition comprising the modified T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

The administration of the modified T cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in these experiments are now described.

Mice: Periostin$^{MCM}$ mice were obtained from the laboratory of Jeffery Molkentin (O. Kanisicak et al., (2016) *Nat Commun* 7, 12260) (Cincinnati Children's). RosaOVA mice provide Cre dependent expression of an intracellular ovalbumin epitope that is presented via MHC I (U. Sandhu et al., (2011) *Nucleic Acids Res* 39, el; M. Cebula et al., (2013) *PLoS One* 8, e68720; A. Ochel et al., (2016) *Cell Mol Immunol* 13, 805-815 20). C57BL/6 mice were obtained from Charles River Laboratories (Wilmington, Mass.). OT-I mice were obtained from The Jackson Laboratory (Bar Harbor, Me.). All animal protocols were approved by the University of Pennsylvania Institutional Animal Care and Use Committee (IACUC).

Reagents and antibodies: Osmotic mini-pumps (Alzet, model 2004) were used for drug delivery. Angiotensin II (A9525-50MG), phenylephrine hydrochloride (P6126-10G), tamoxifen (T5648-1G), and corn oil (C8267) were obtained from Millipore Sigma. Picro Sirius Red Stain Kit (ab150681), Anti-Fibroblast activation protein, alpha antibody (ab207178), and GFP (ab6673) were obtained from Abcam. Sterile saline (0.9% sodium chloride, 00409488850) was obtained from Hospira (Lake Forest, Ill.).

Animal Experiments: All mice used in experiments were adult males between 10 and 14 weeks of age. Angiotensin II (1.5 µg/g/day) and phenylephrine (50 µg/g/day) or saline (0.9% sodium chloride) were continuously administered through osmotic mini-pump (Alzet, 2004) for 28 days. Periostin$^{MCM}$ mice were induced for Cre expression by intraperitoneal injections of 100 µl of tamoxifen in corn oil (20 mg/ml). Injections were administered on alternating days for 1 week, and then weekly afterward until sacrificed. Adoptive transfer of T cells was administered through tail vein injection. Echocardiography was performed under isoflurane anesthesia using a Vivid FiVe ECHO system (GE Medical Systems).

Adoptive T cell transfer: Mouse T cells expressing a CAR construct specific for mouse FAP (containing the scFv fragment from the specific mouse FAP antibody (clone 73.3) (L. C. Wang et al., (2014) *Cancer Immunol Res* 2, 154-166) coupled to the human CD3Z and CD28 cytoplasmic domains along with a small peptide that conferred resistance to adenosine and prostaglandin E2 mediated suppression (27) or GFP were used. Infective particles were generated from the supernatants of "Phoenix" packaging cells (Allele; Phoenix Eco Cells Line #ABP-RVC-10002) transfected with retroviral vector plasmid and helper plasmids using Lipofectamine 2000 (Invitrogen), as previously described (L. C. Wang et al., (2014) *Cancer Immunol Res* 2, 154-166). T cells were cultured in RPMI 1640 supplemented with 10% FBS, 100 U/mL penicillin, 100 µg/mL streptomycin sulfate, 1 mM Pyruvate, and 50 µM beta-mercaptoethanol. Primary murine T cells were isolated as suggested by the manufacturer (Miltenyi Biotec) from the spleens of mice and incubated in 12-well plates [2×10$^6$ cells/well in 2 ml T-cell media with 50 U/mL mouse interleukin (IL)-2 and Dynabeads Mouse T-Activator CD3/CD28 (Gibco, #11453D) in a 1:1 ratio]. After 48 hours, cells were plated in a 24-well plate coated with retrovirus and 5 µg/cm$^2$ of Retronectin (Takara, #T100B). Prior to plating T cells, a Retronectin-coated 24-well plate was centrifuged without braking at room temperature for 1 hour at 1000 g 20 with 1 ml/well crude viral supernatant. After overnight incubation, cells were expanded with 50 U/mL of IL-2 for 48 hours. The transduction efficiency with muFAP-CAR-RIAD (FAP-CAR T-cells) or FAP-GFP-CAR was assessed after transduction. 10$^7$ CAR T cells were injected per mouse.

For the OVA experiments, cells were obtained from C57BL/6 OT-I mouse spleens and purified using the mouse CD8a+ T Cell Isolation Kit (Miltenyi Biotec, 130-104-075). Purity was assessed by flow cytometry. 5×10$^6$ CD8+ T cells were adoptively transferred to mice 1 week after injury.

Histology and Immunohistochemistry: Mouse and human tissue samples fixed overnight in 2-4% paraformaldehyde and dehydrated through an ethanol series. All samples were paraffin-embedded and sectioned. Hematoxylin and eosin (H&E), and Masson's trichrome staining were completed using a standard protocol. Pricro Sims Red staining was completed using a kit (Abcam, 150681) as per instructions. Briefly, sections were deparaffinized, incubated with Pircro Sirius Red for 1 hour, washed in acetic acid solution, washed in absolute alcohol, cleared with xylene, and mounted. Slides were digitally scanned at 20× and analyzed via color deconvolution using ImageScope (Apiero) software. At least eight distinct sections were quantified for percent fibrosis for each mouse in each condition.

Human Cardiac Expression data: LV cardiac tissues were obtained from the Myocardial Applied Genomics Network (MAGNet; www.med.upenn.edu/magnet). All subjects donating tissue provided consent under an approved IRB protocol, and provided clinical information that is confidentially linked to the specimens by a study number. LV free-wall tissue was harvested at the time of cardiac surgery from subjects with heart failure undergoing transplantation and from unused donor hearts. The heart was perfused with cold cardioplegia prior to cardiectomy to arrest contraction and prevent ischemic damage. Tissue specimens were then obtained and frozen in liquid nitrogen and stored at −80° C. until used.

Total RNA was extracted from human cardiac tissue samples using the miRNeasy Kit (Qiagen) including DNAse treatment. For RNA-seq, library prep was conducted using Illumina truSeq stranded mRNA kit followed by the Nugen Ovation amplification kit. Resultant fastq files were assessed for quality control using the FastQC program. Fastq files were aligned against the mouse reference genome (hGRC37/Hg19) using the STAR aligner (Dobin et al., (2013) *Bioinformatics*, Volume, 29:1, 15-21). Duplicate reads were flagged using the MarkDuplicates program from Picard tools. Per gene read counts for Ensembl (v75) gene annotations were computed using the R package with duplicate reads removed. Gene counts represented as counts per million (CPM) were first nominalized using TMM method in the edgeR R package and genes with 25% of samples with a CPM<1 were removed and deemed low expressed. The data was transformed using the VOOM function from the limma R package (C. W. Law, et al. (2014) *Genome Biol* 15, R29. Differential gene expression was performed using a linear model with the limma package.

Statistics: All data are represented as the mean±standard error of the mean (SEM). Differences between multiple groups were compared with one-way analysis of variance (ANOVA). Significant ANOVA results were further analyzed by Tukey's multiple comparisons test. *P<0.05, P<0.01, *P<0.001, ns=not significant.

The results of the experiments are now described.

Example 1

Reversal of Cardiac Fibrosis via CAR T-Cell Immunotherapy

The present invention relates to the use of engineered immune cells for the treatment of cardiac diseases and disorders. Mouse models of hypertensive heart disease, diastolic dysfunction and heart disease were used to test the engineered elimination of fibrosis in the heart using modified immune cells targeted to antigens specific for activated fibroblasts.

Previous studies have demonstrated that genetic ablation of cardiac fibroblast can reduce cardiac fibrosis and rescue cardiac function in mouse models of angiotensin induced hypertensive heart disease and coronary artery ligation induced myocardial infarction (Kaur et al., Circ Res. 2016 Jun. 10; 118(12):1906-17).

In the present study, using a mouse model of heart disease, mice were treated with a chimeric antigen receptor (CAR) that targets cardiac fibroblasts. More specifically, the CAR targets fibroblast activation protein (FAP), which is specific for activated fibroblasts. Following treatment with the FAP-CAR, cardiac function, morphology, and fibrosis were tested in the mice. CAR-T cells against FAP were previously developed and shown to reduce fibrosis in pancreatic tumors (International Application No. WO2014055442, incorporated in its entirety herein). The FAP-CAR T cells were also shown to be safe and have minimal off-target effects. However, FAP-CAR T cells have not been investigated to date for use in treating heart disease. This novel application of using FAP-CAR T cells to treat heart disease is demonstrated for the first time herein.

Fibroblast activation protein alpha expression was identified in activated fibroblasts after myocardial infarction in rat and human hearts (Tillmanns et al. J Mol Cell Cardiol. 2015 October; 87:194-203). FAP expression in injured mouse heart was largely unknown. FAP antibodies work well in humans, rat, and others, and for frozen mouse tissue. However, until now, no FAP antibody had been shown to work well in paraffin embedded mouse tissue for immunohistochemistry (IHC) or immunofluorescence (IF).

Figure 1B:
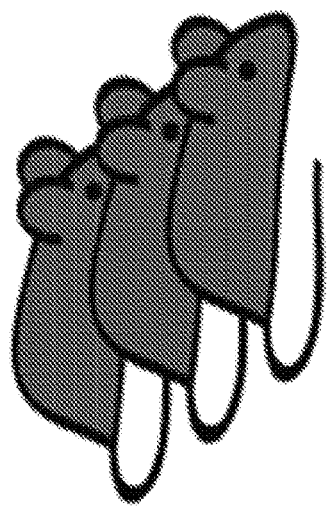
Figure 1B:
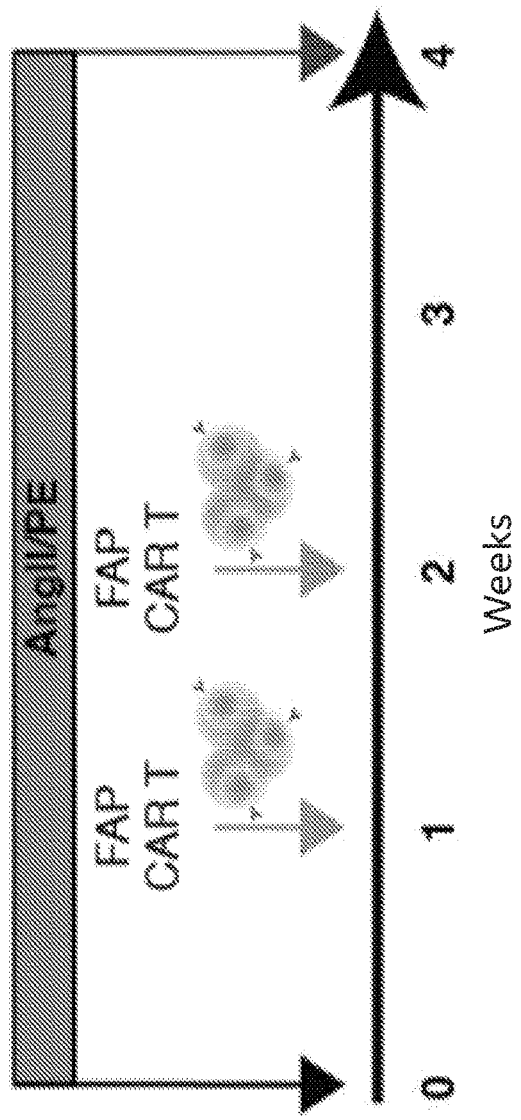
Figure 1C:
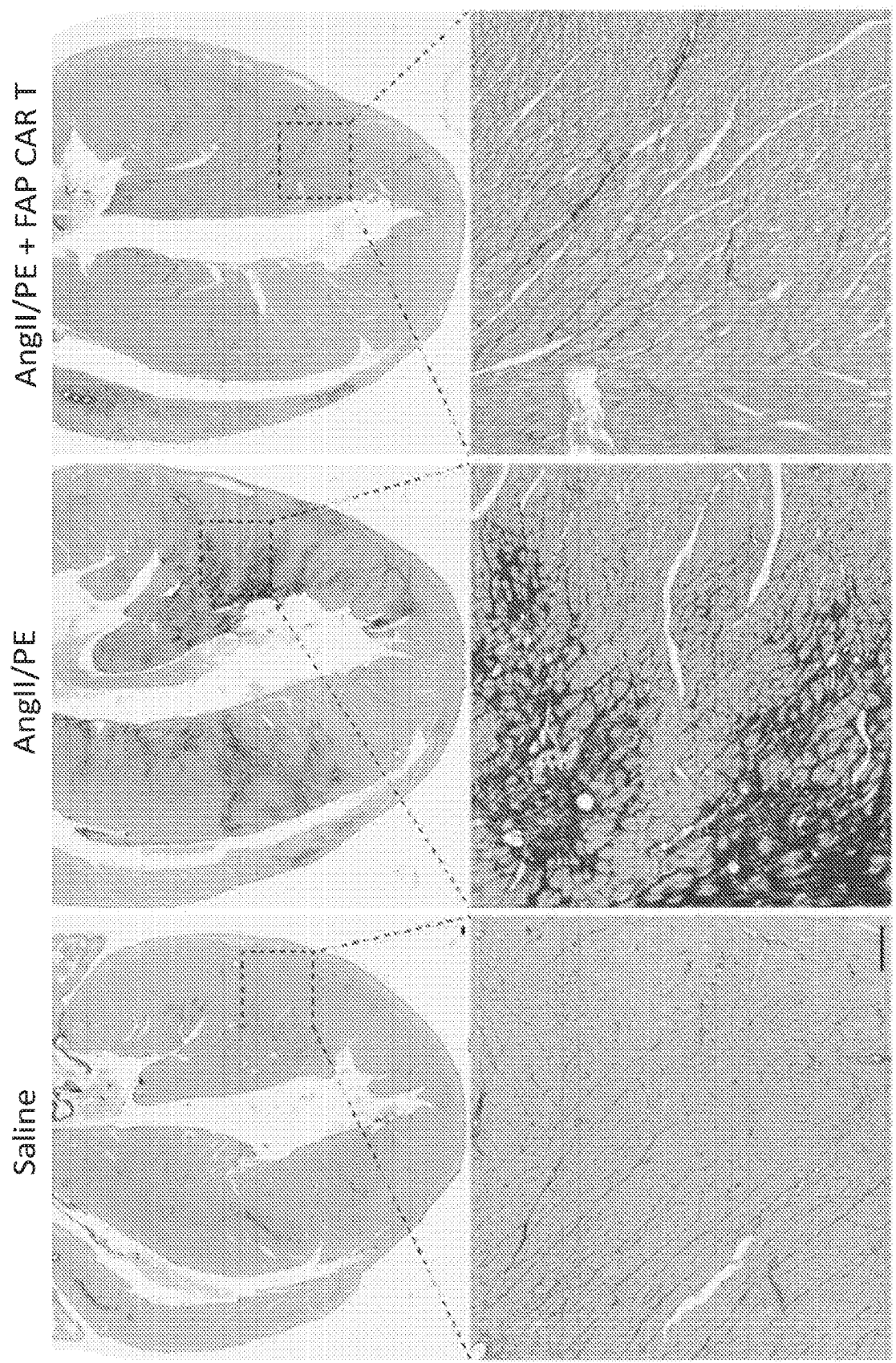
Figure 1D:
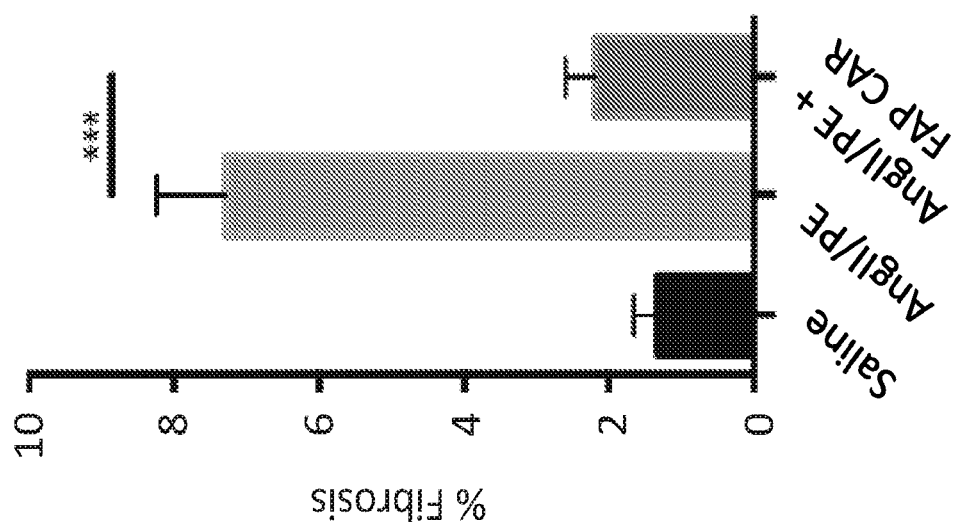
Figure 1E:
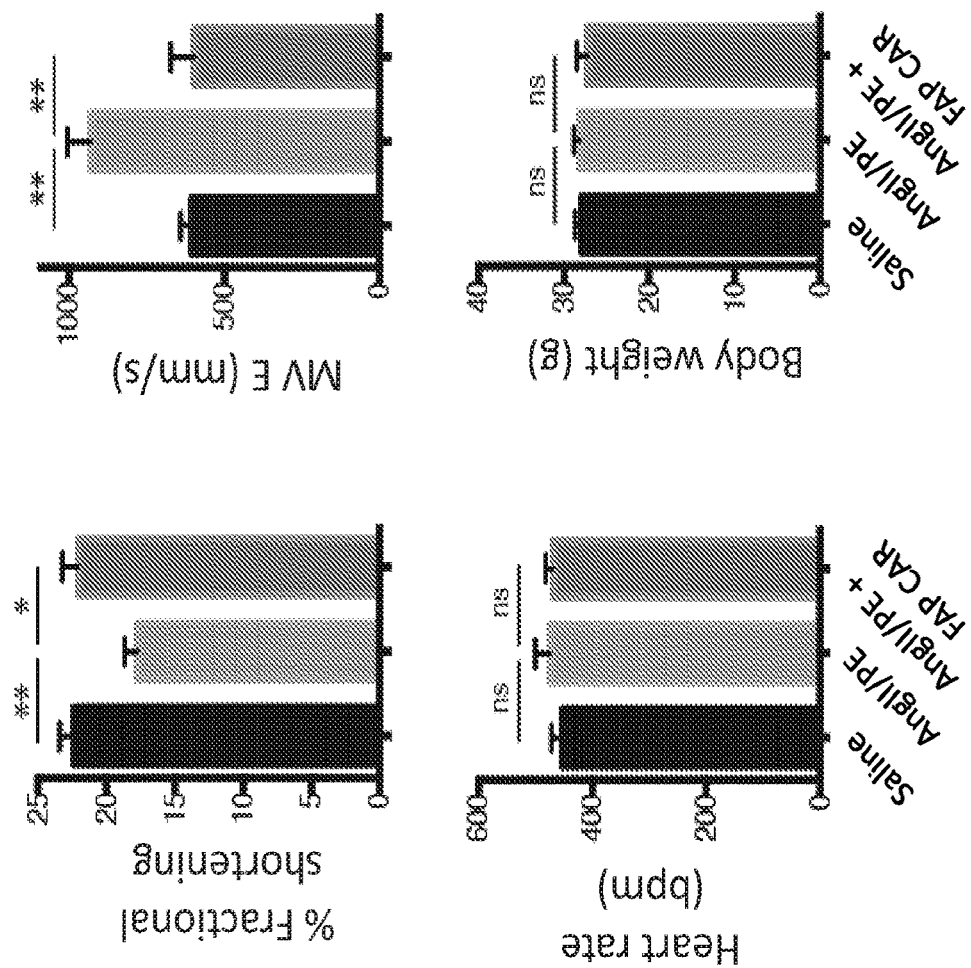
Figure 2:
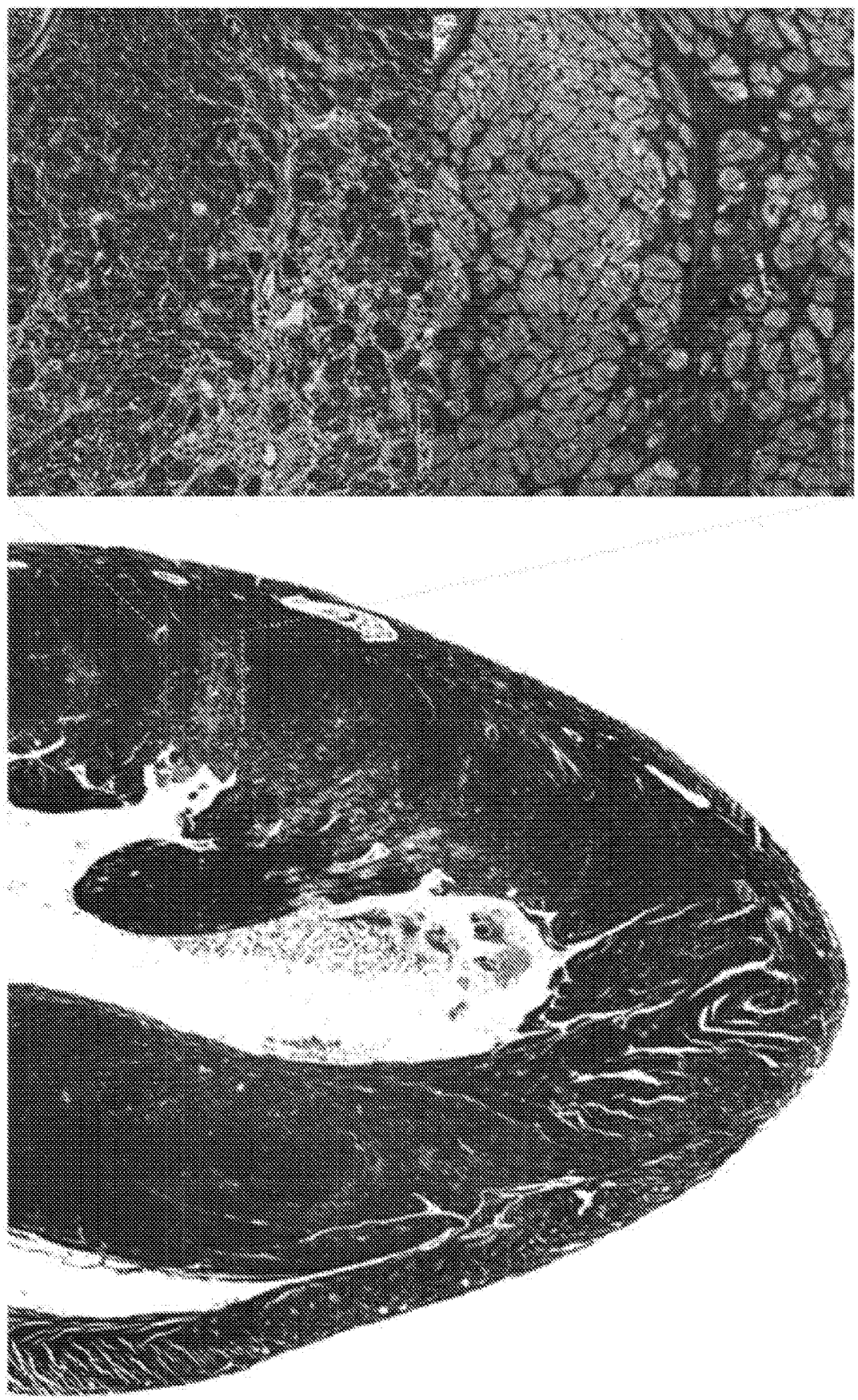
FIG. 2 illustrates Masson's trichrome stain for fibrosis (blue; left; right, top) and immunohistochemistry for FAP (right, bottom) in WT coronal heart sections 2 weeks after continuous AngII/PE treatment. Staining and immunohistochemistry were performed in adjacent sections. Right insets depict higher magnification of left ventricular free-wall. Scale bars=100 μm.
Figure 3:
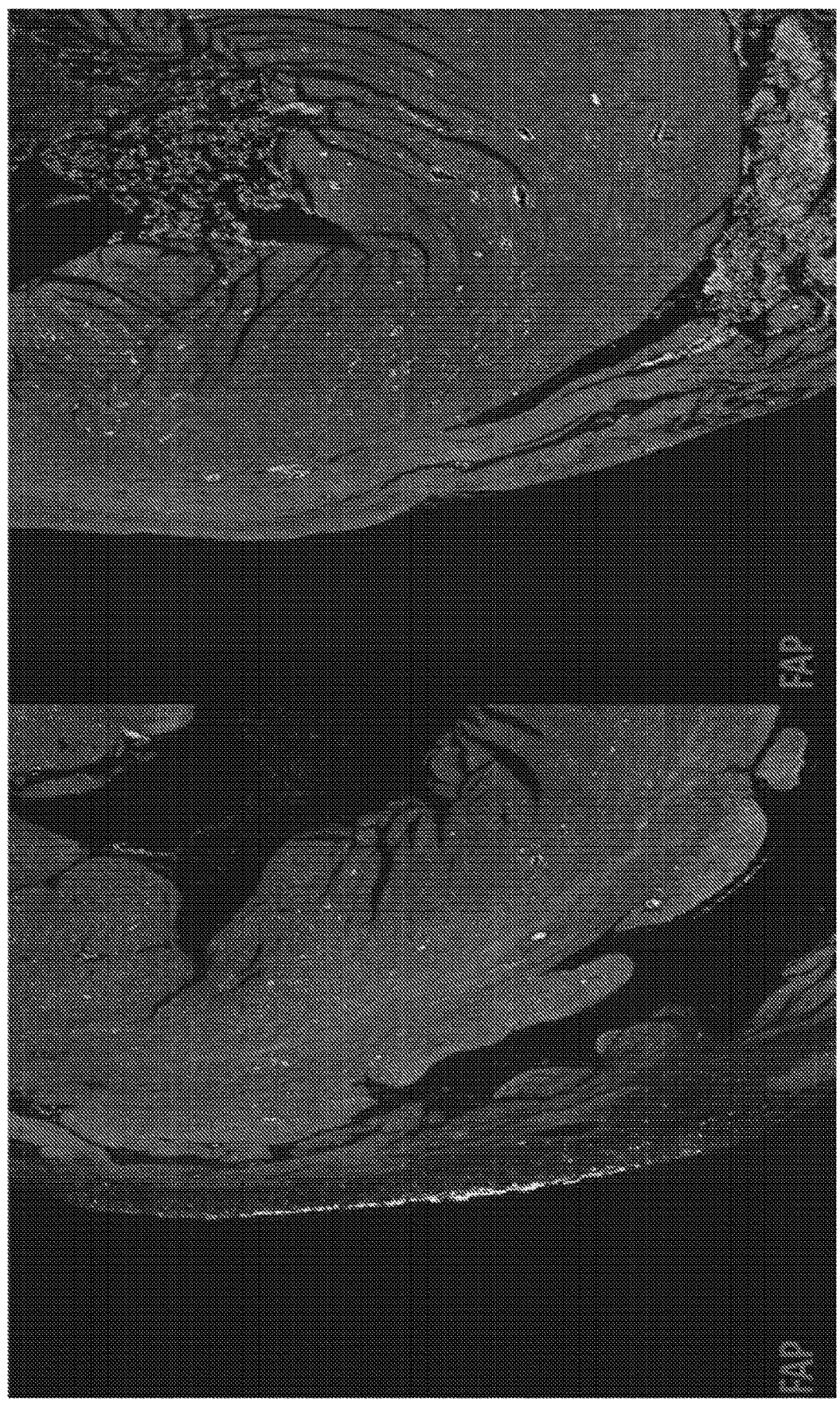
FIG. 3 illustrates fibroblast activation protein (FAP) expression 1 week after myocardial infarction.
Figure 4:
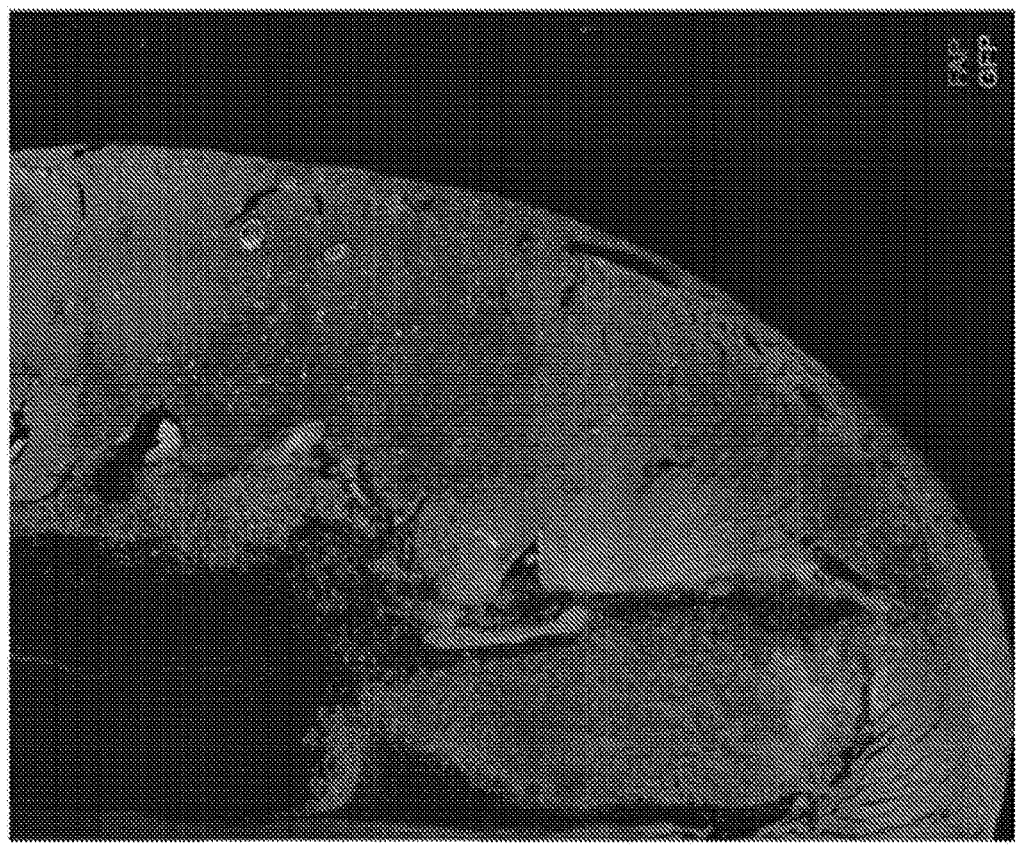
FIG. 4 illustrates immunohistochemistry for FAP and GFP on the left ventricular free wall of mouse heart coronal sections. WT C57Bl/6 mice were treated with (right) or without (left) AngII/PE for 1 week and injected with FAP-GFP-CAR T cells and sacrificed 1 day later.
Figure 4:
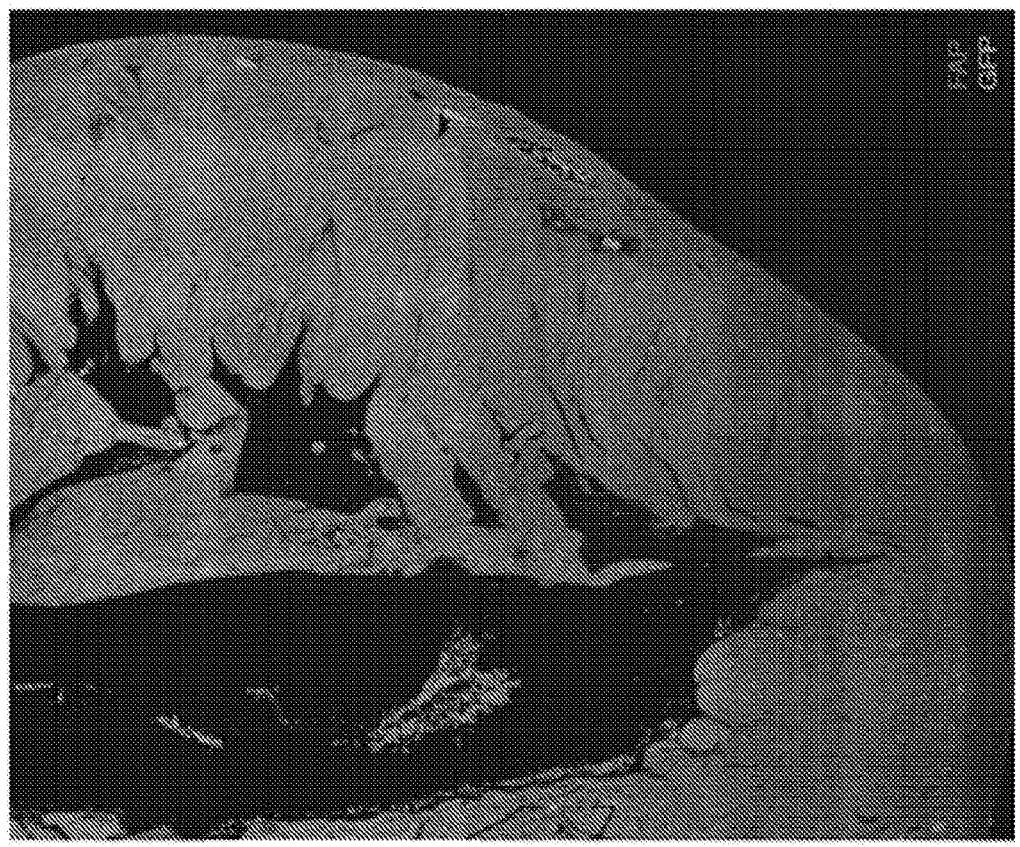
Figure 5A:
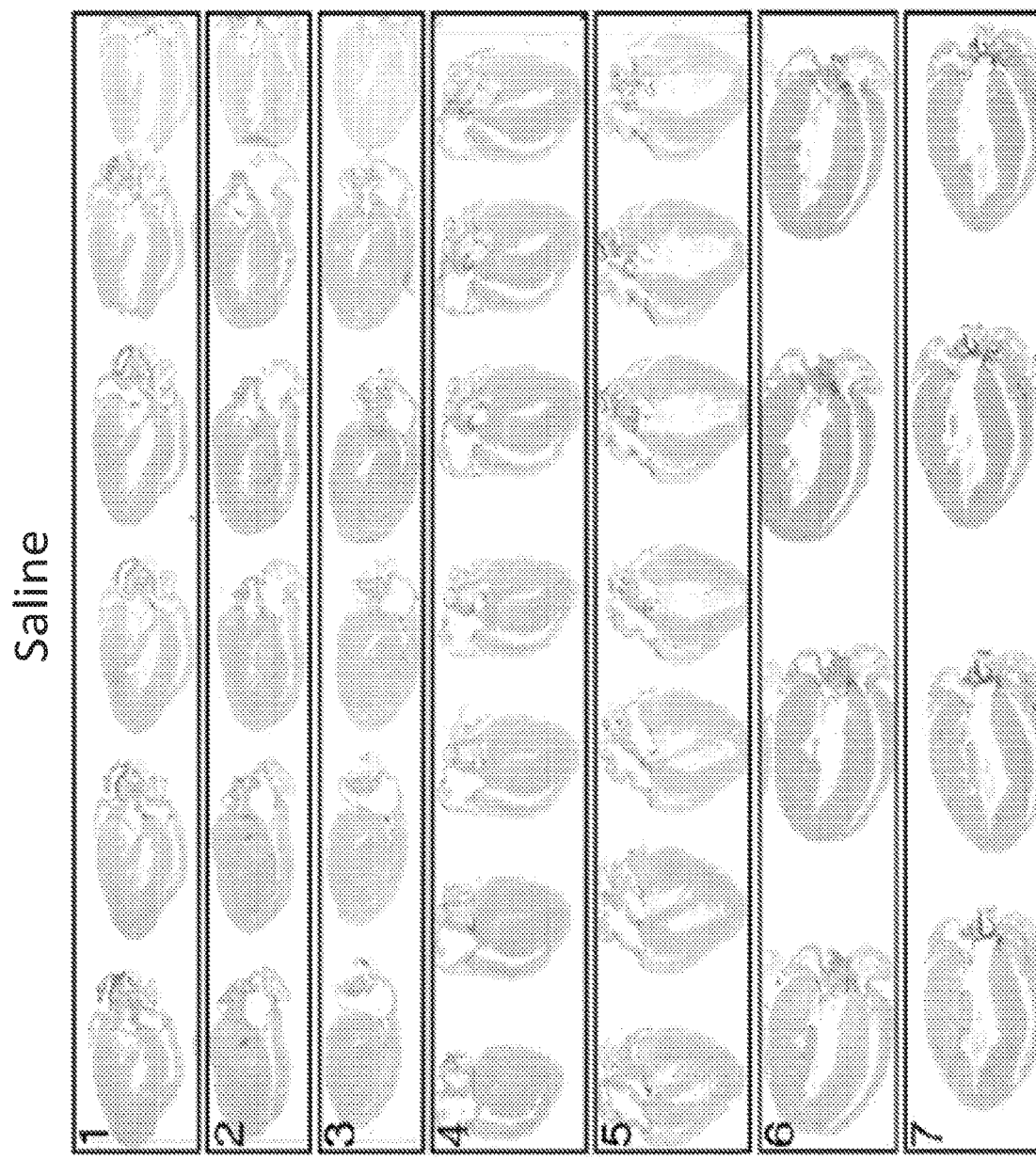
FIGS. 5A-5C illustrate Picro-Sirus Red staining of hearts from 7 individual mice (#1-7) in each condition, treated for 4 weeks with either saline, AngII/PE, or AngII/PE+FAP-CAR T cells to assess for fibrosis.
Figure 5B:
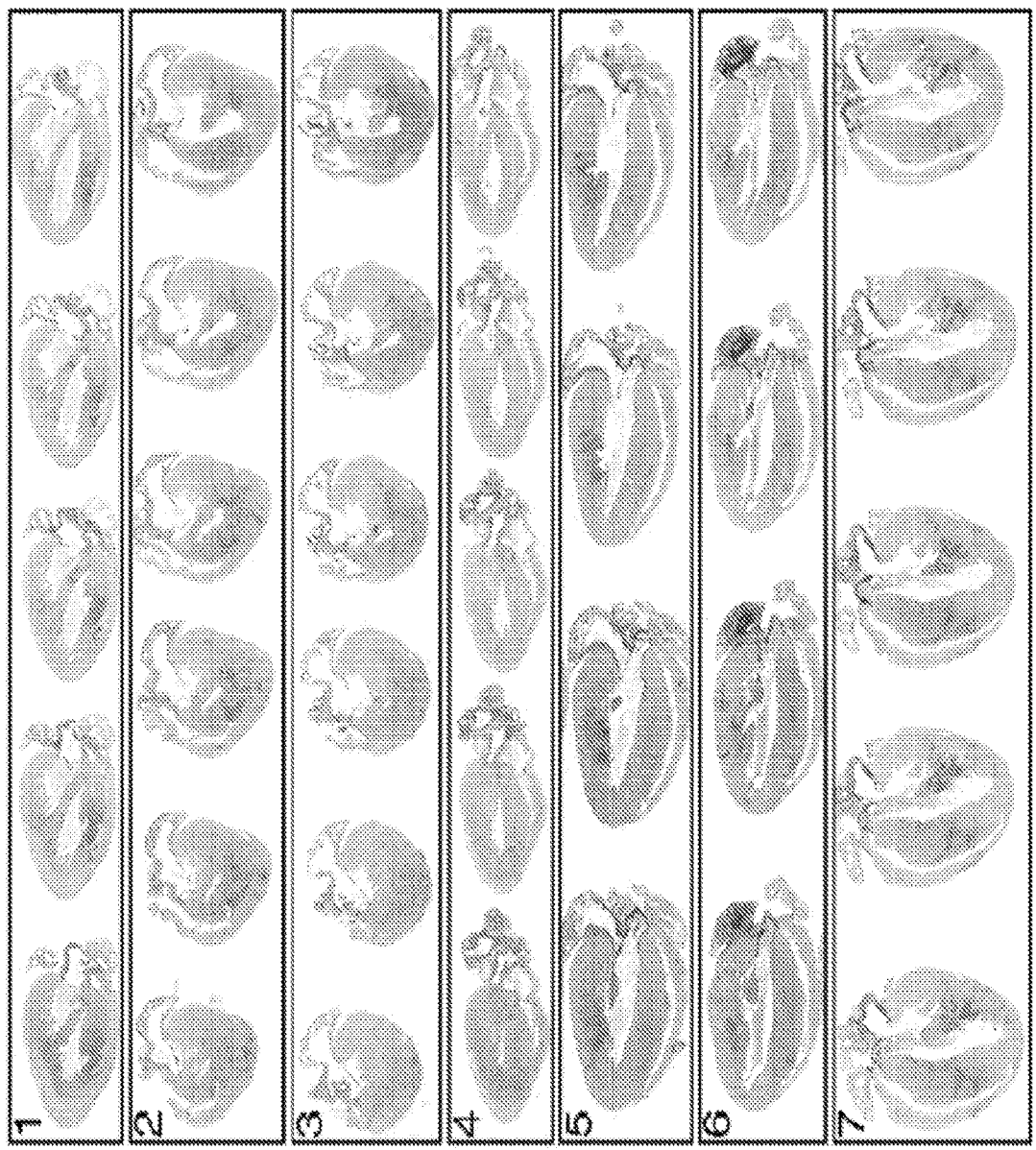
Figure 5C:
Figure 6A:
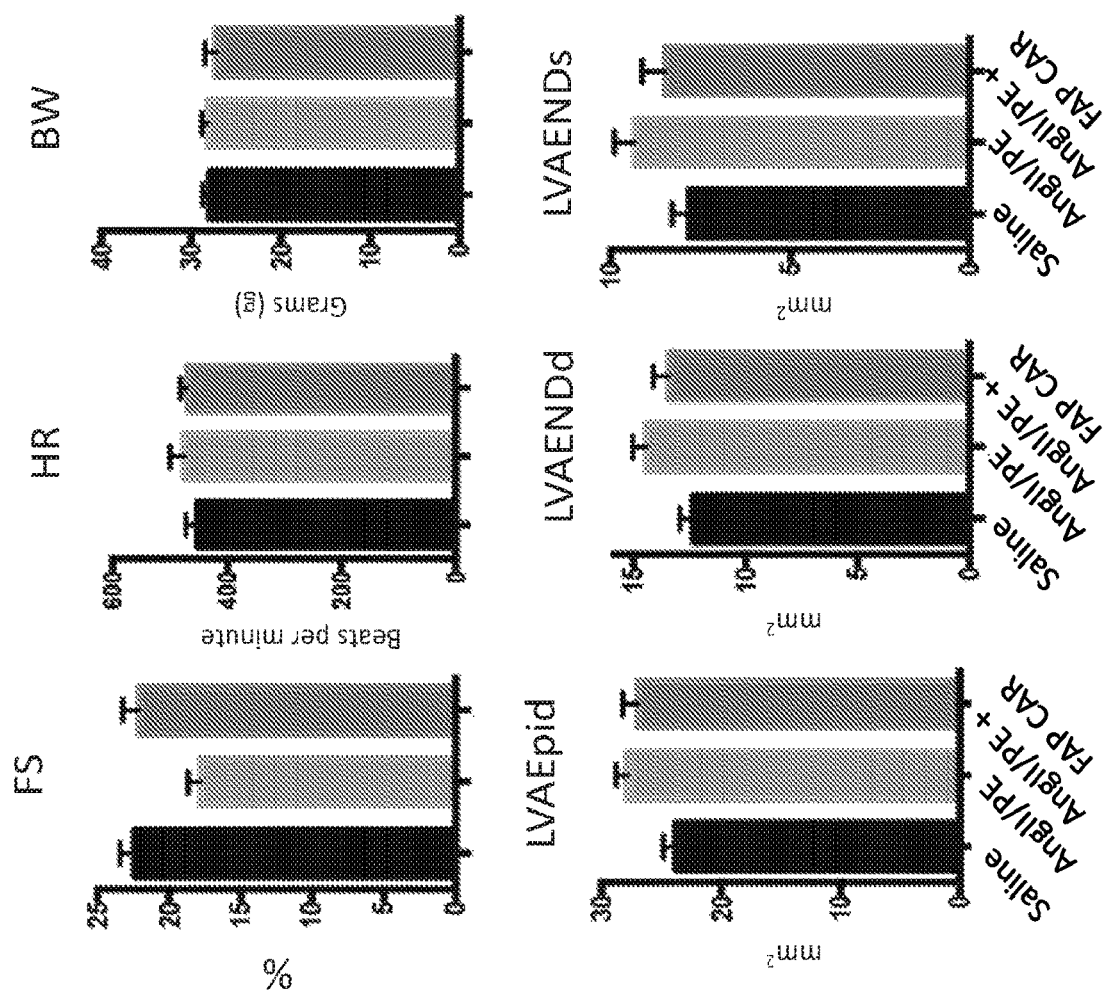
FIGS. 6A-6C illustrate results from echocardiogram examination of C57Bl/6 mice treated for 4 weeks with either saline, AngII/PE, or AngII/PE+FAP-CAR T cells.
Figure 6B:
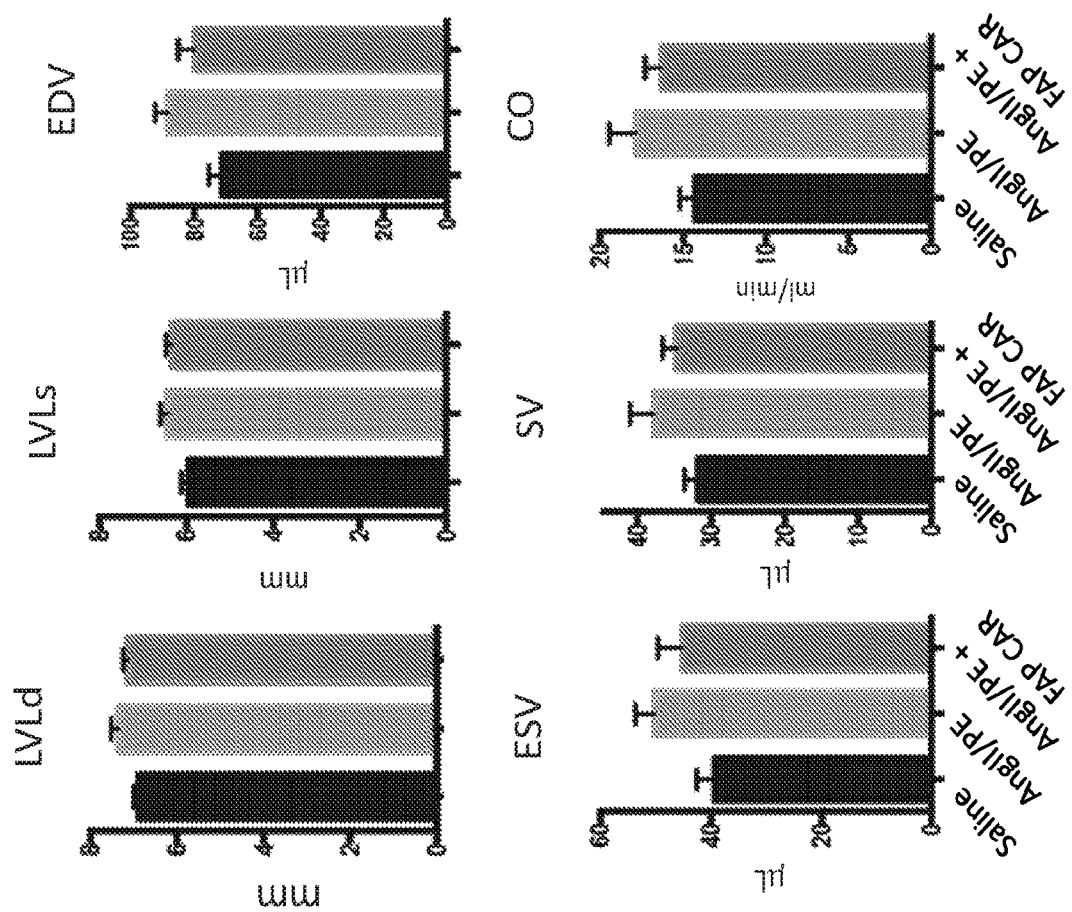
Figure 6C:
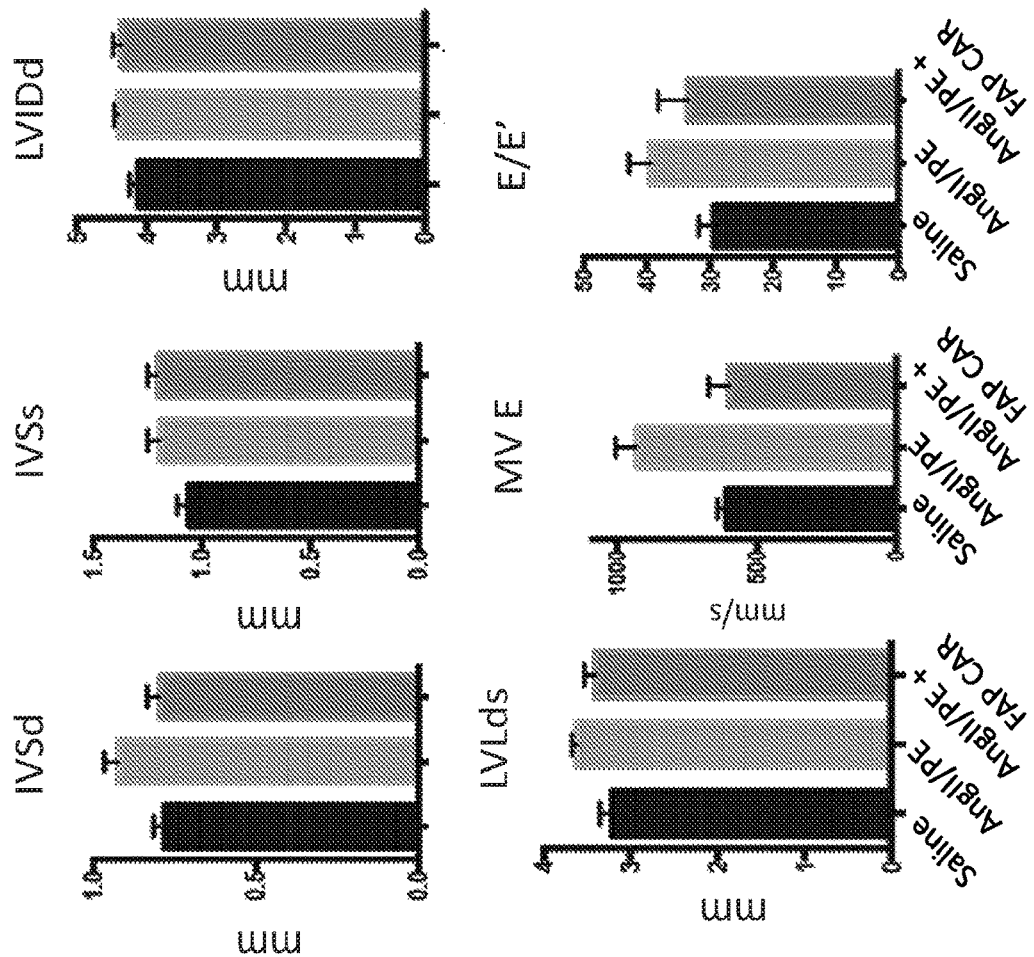
Figure 7A:
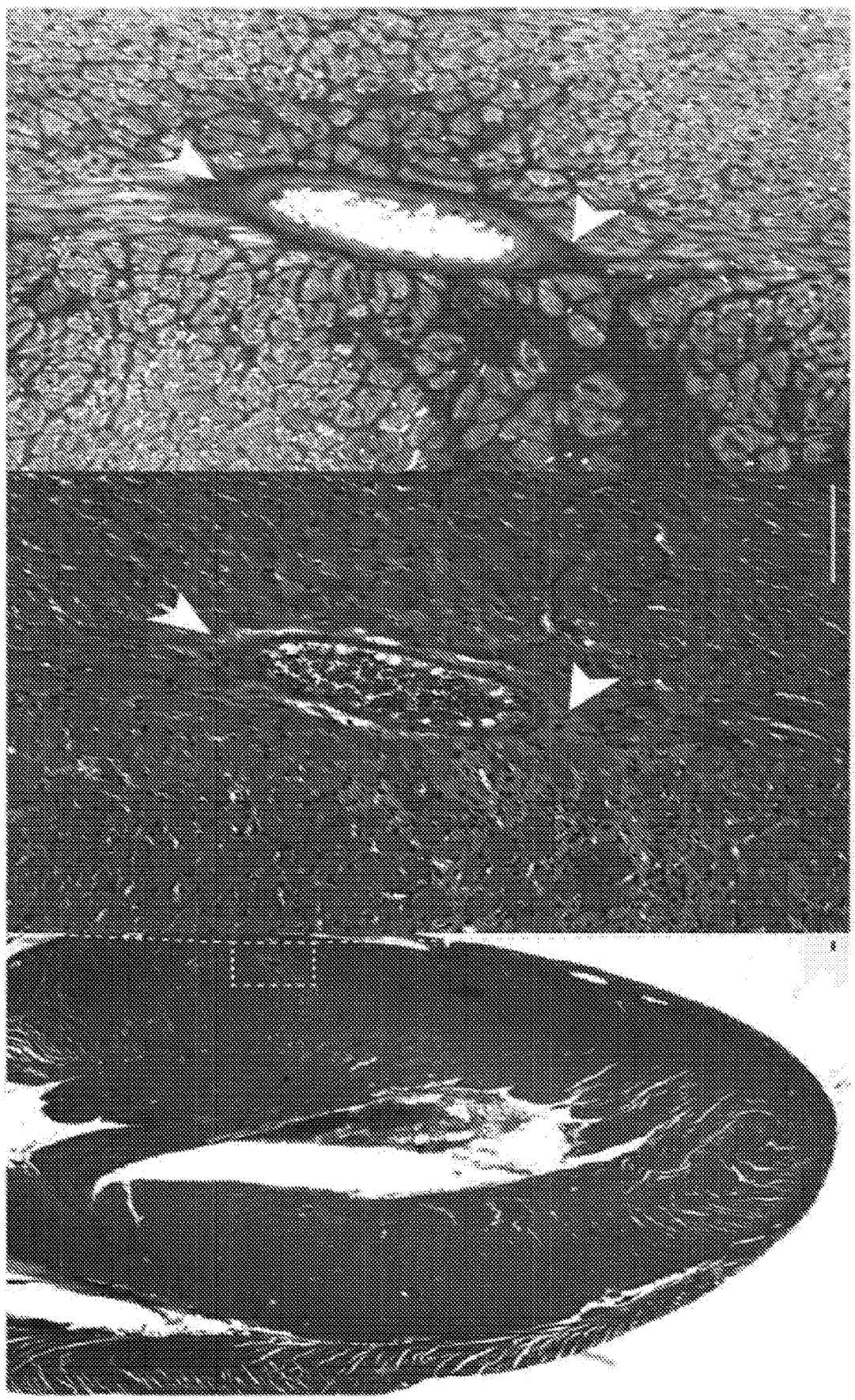
FIGS. 7A-7B illustrate partial rescue of both systolic and diastolic cardiac function in injured mice treated with FAP-CAR T cells.
Figure 7B:
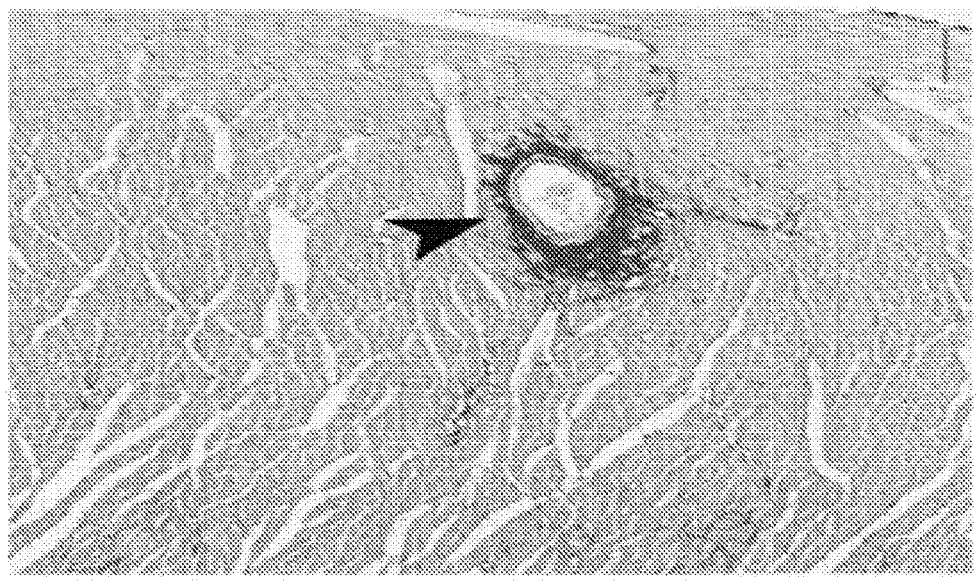
Figure 7B:
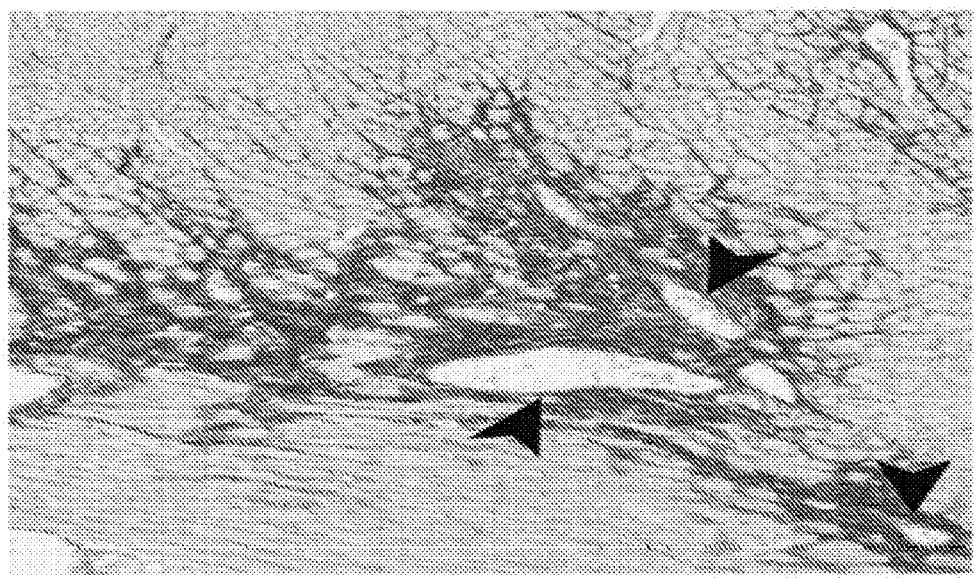
Figure 7B:
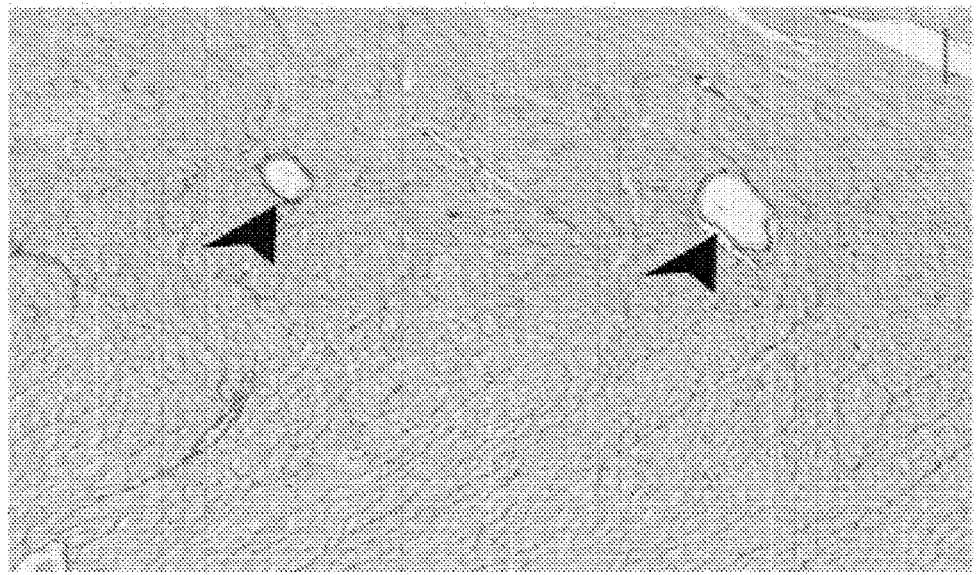
Figure 8:
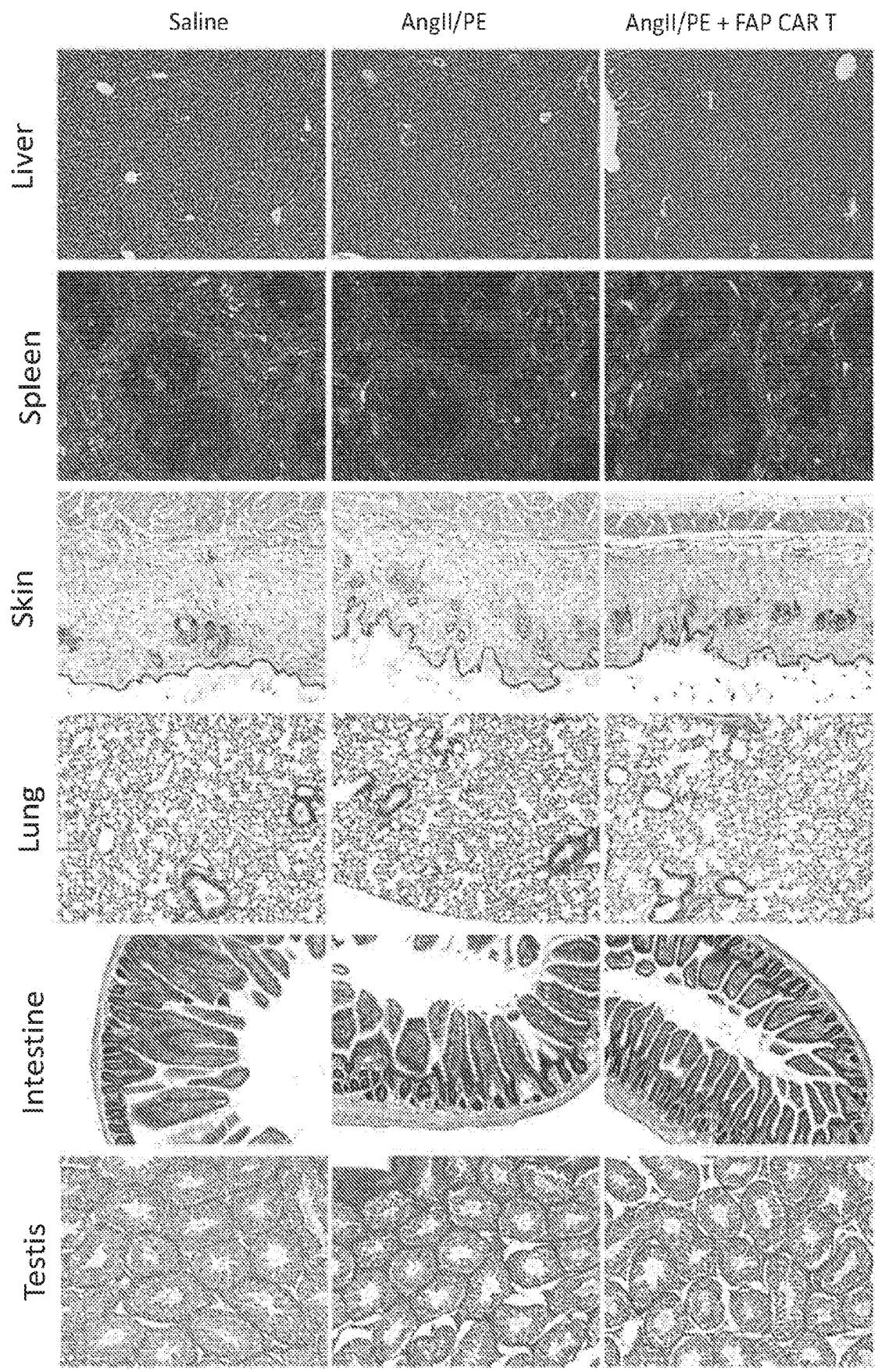
FIG. 8 illustrates H&E staining of various tissue sections from mice treated for 4 weeks with either saline, AngII/PE, or AngII/PE+FAP CAR T cells.

To test the feasibility of FAP as an endogenous CF target for immunotherapy, an AngII/PE model of cardiac injury and fibrosis in mice was used. It was confirmed that FAP is expressed by activated cardiac fibroblasts in this model. Immunohistochemistry showed that FAP was not detectable in control hearts, but was apparent on activated fibroblasts after 1 and 2 weeks of AngII/PE exposure (FIG. 1A, FIG. 2). FAP expression was also seen in sections taken from a mouse 1 week post coronary artery ligation induced myocardial infarction compared to sham (FIG. 3, left panel). To target and deplete FAP-expressing cardiac fibroblasts in this model, FAP-CAR T cells were adoptively transferred 1 and 2 weeks after AngII/PE (FIG. 1B). A second injection of FAP-CAR T cells was administered in this set of experiments due to the short half-life of mouse FAP-CAR T cells that were previously observed in tumor models. FAP-CAR Tcells infiltrated the myocardium and co-localized with FAP expressing CFs within 1 day of adoptive transfer (FIG. 4). By 4 weeks, there was a significant reduction of cardiac fibrosis in injured mice that had been treated with the FAP-CAR T cells when compared to controls (FIG. 1C-1D). Widespread cardiac fibrosis was evident in each of the control mice that were exposed to AngII/PE, while fibrosis was reduced in all 7 of 7 (and nearly eliminated in 5 of 7) AngII/PE exposed mice that were treated with FAP-CAR T cells (FIG. 5A-5C). Along with the reduction in fibrosis, a partial rescue of both systolic and diastolic cardiac function was observed in injured mice treated with FAP-CAR T cells when compared to controls (FIGS. 1E-1F, FIGS. 6A-6C). Interestingly, persistence of perivascular fibrosis was observed after treatment, consistent with the lack of FAP expression in perivascular fibroblasts (FIGS. 7A-7B) induced by AngII/PE. Importantly, with regard to potential therapeutic use, histological effects of FAP-CAR T therapy were undetectable in numerous other organs or tissues (FIG. 8). FAP-CAR T cells have been administered to animals by others to target tumor stromal cells without untoward effects.

Figure 9B:
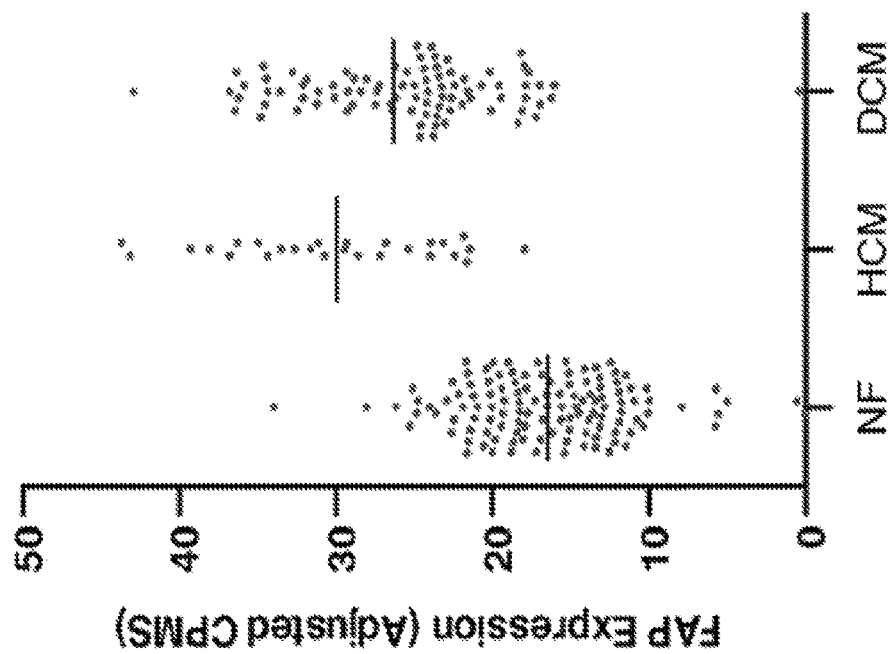
FIGS. 9A-9C illustrate human cardiac fibroblast targets in disease.
Figure 9A:
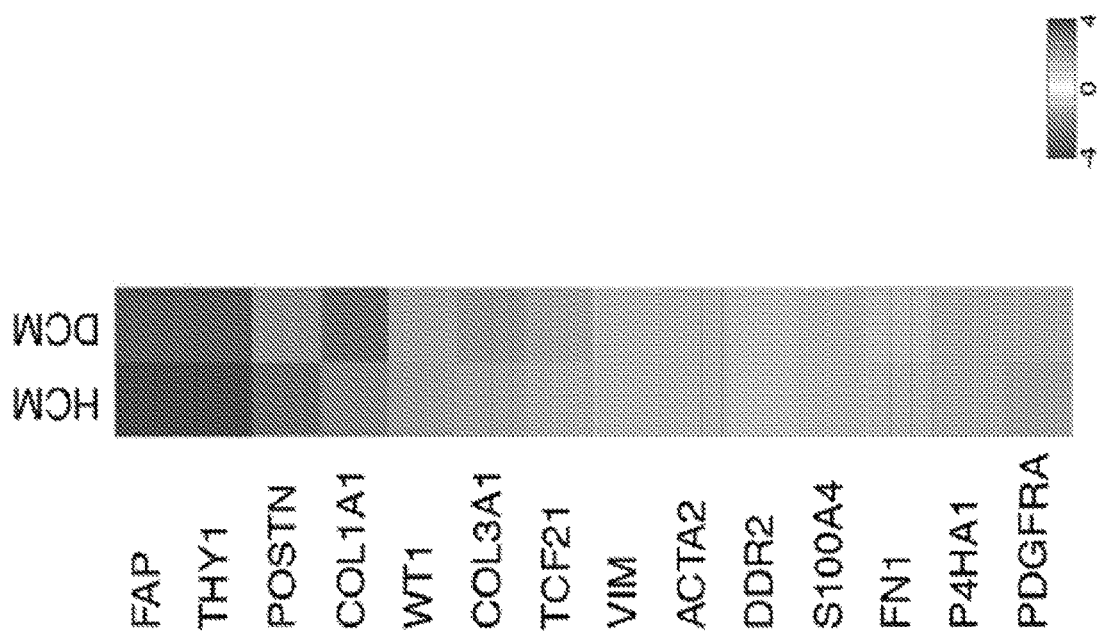
Figure 9C:
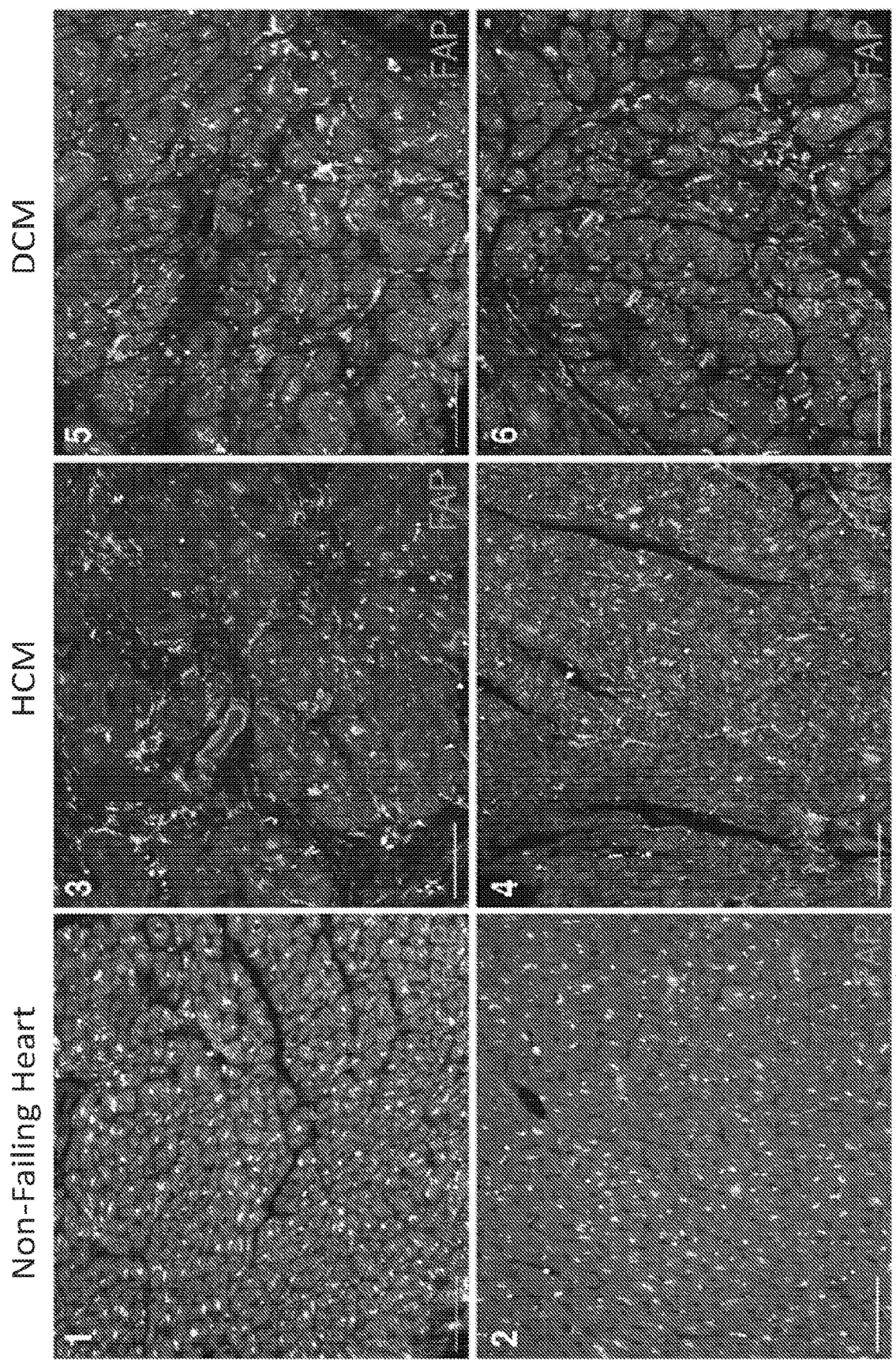

Having demonstrated that immunologically targeting and depleting activated cardiac fibroblasts is possible in mice, this set of experiments sought to identify endogenous proteins/antigens expressed by human activated cardiac fibroblasts, but not by quiescent fibroblasts or other critical cell types, that could be specifically targeted by engineering (or genetically modifying) T cells to recognize such an antigen. Gene expression data from an RNAseq database compiled from samples of 238 human heart transplant donor and recipient left ventricular (LV) tissue was analyzed. Several fibroblast-specific genes were found to be upregulated in myocardium from patients with either hypertrophic cardiomyopathy (HCM) or dilated cardiomyopathy (DCM) when compared to control donor hearts (FIG. 9A, FIG. 10). To be considered a good target for cell-based immunotherapy, an antigen should be specifically expressed in diseased cells, have minimal-to-no expression elsewhere in the body, and ideally be recognizable on the cell surface. Topping the list with regard to fold change, is fibroblast activation protein alpha (FAP). FAP is a cell surface glycoprotein that was found to be expressed at significantly higher levels in HCM and DCM samples when compared to control hearts (FIG. 9B). FAP expression has been previously observed in human hearts following acute myocardial infarction. This finding was extended by showing by immunohistochemistry of human LV tissue from failing DCM and HCM hearts that FAP is robustly expressed by pathologic cardiac fibroblasts (and not by myocytes) (FIG. 9C), while FAP expression is not detected in normal human hearts. Thus, FAP is a promising candidate for targeting of pathological cardiac fibroblasts in humans.

The work disclosed herein demonstrates that cardiac fibrosis can be effectively treated in mice with engineered T cells and targeted immunotherapy. When FAP-expressing pathologic cardiac fibroblasts were reduced or eliminated, cardiac function was improved. Moreover, FAP is expressed in human hearts by fibroblasts associated with both hypertrophic and dilated cardiomyopathy. In certain embodiments, modified T cells can be engineered with a "kill-switch" to limit time of survival so as to minimize ongoing side-effects and "off-target" effects. Herein, it was demonstrated that the "immunorevolution" can extend beyond oncology to impact one of the most common forms of human morbidity and mortality: heart disease.

Example 2

Reversal of Cardiac Fibrosis via TCR Based Immunotherapy

Figure 11A:
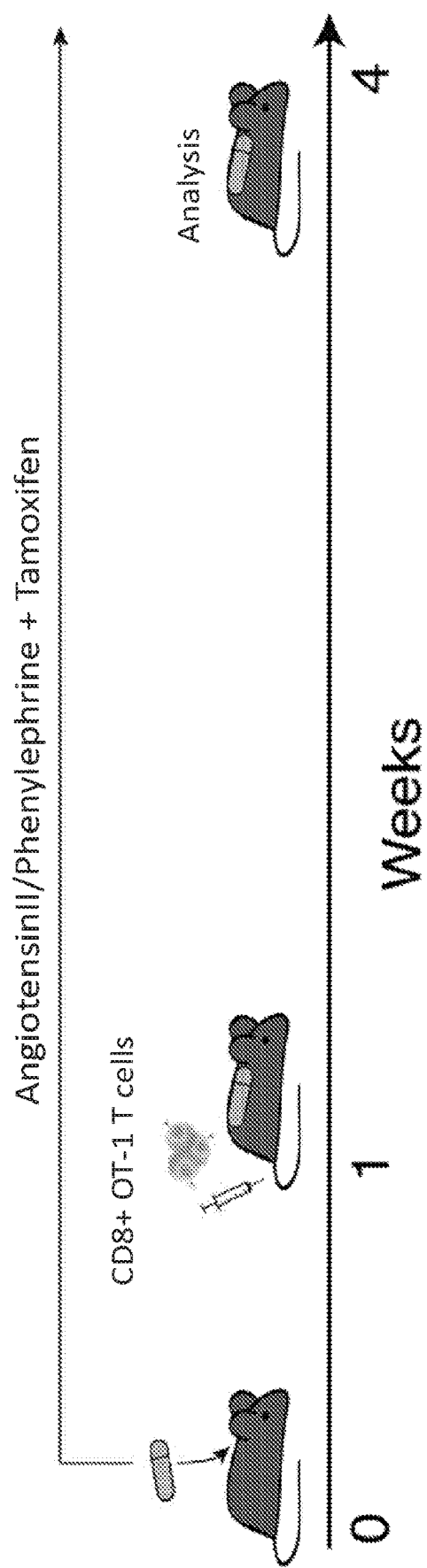
FIGS. 11A-11C illustrate the finding that redirected T cells can ablate cardiac fibroblasts.
Figure 11B:
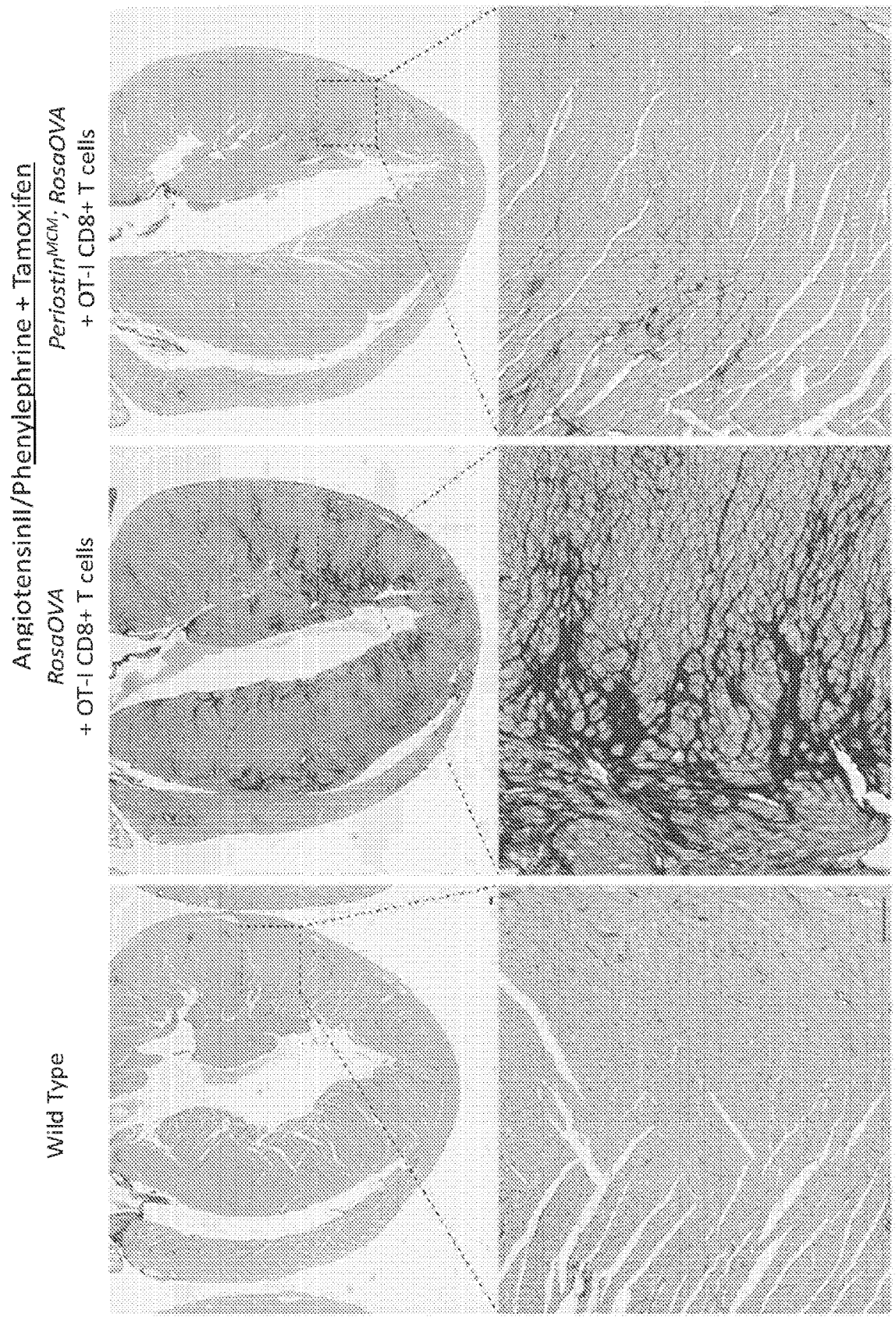
Figure 11C:
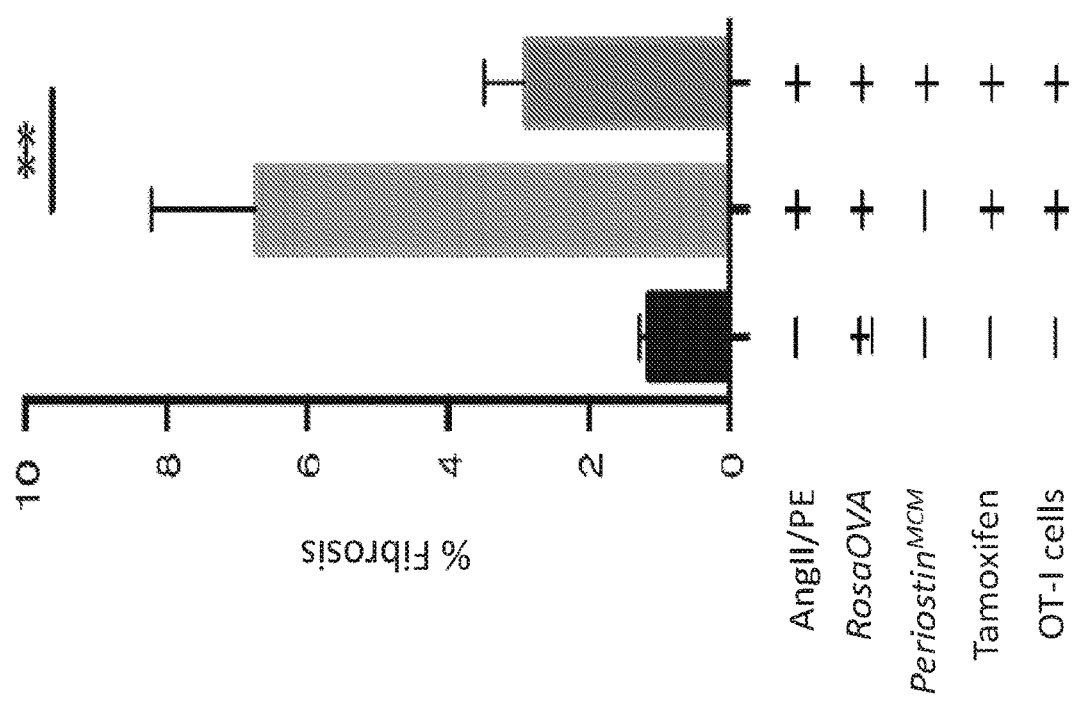
Figure 12:
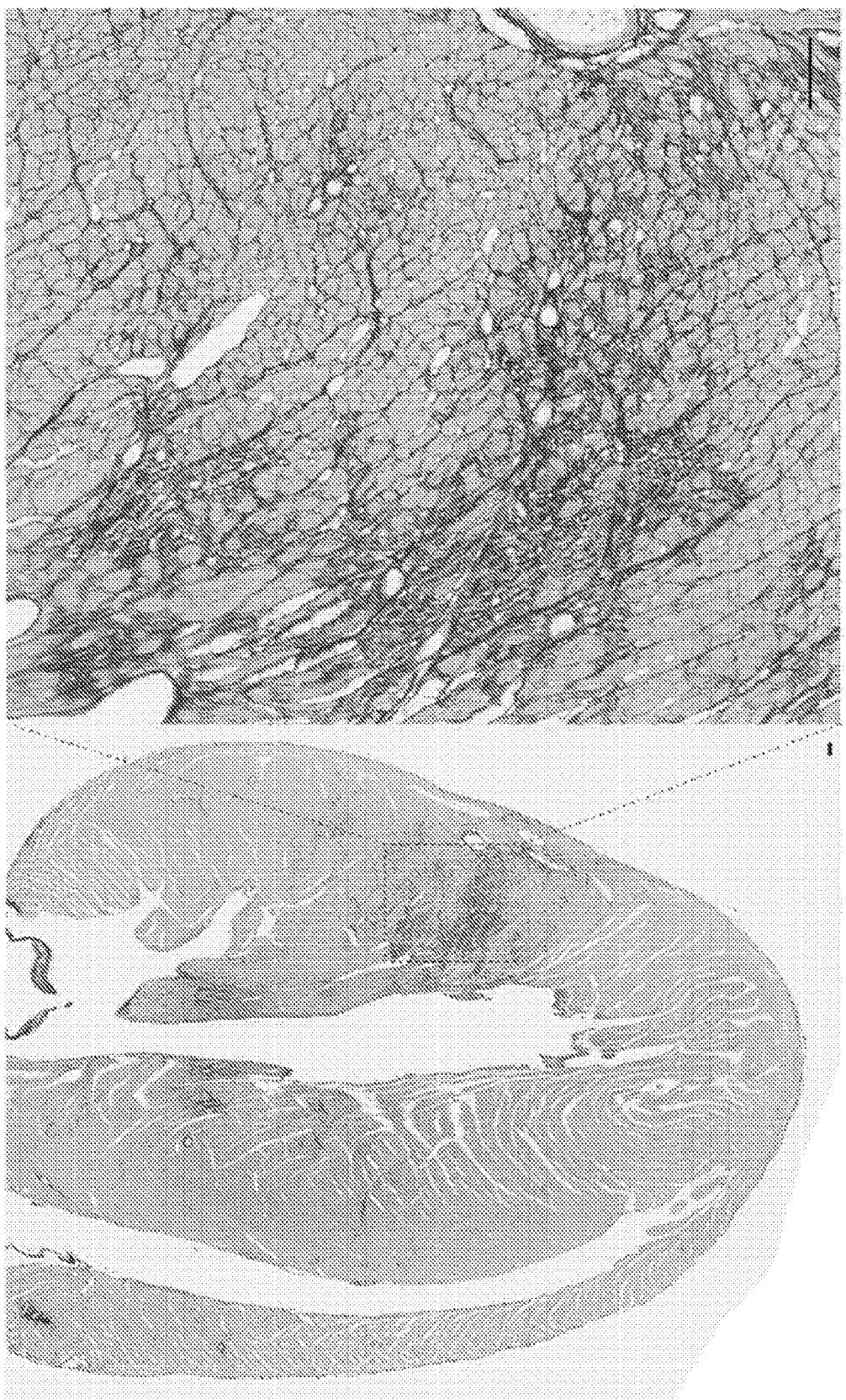
FIG. 12 illustrates Pircro-Sirius Red staining for cardiac fibrosis in a heart coronal section from a Periostin$^{MCM}$; RosaOVA mouse treated with AngII/PE and tamoxifen for 1 week. High powered field of left ventricular free-wall is shown on the right. Scale bars=100 μm.
Figure 13A:
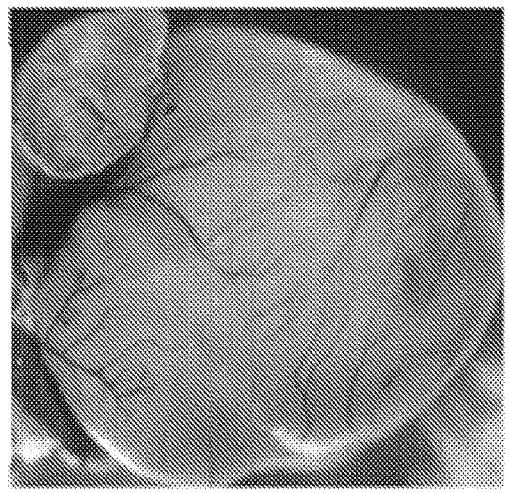
FIGS. 13A-13B illustrate the finding that cardiac hypertrophy is partially rescued after after OT-I T cell adoptive transfer in OVA;Postn$^{MCM}$ mice.
Figure 13A:
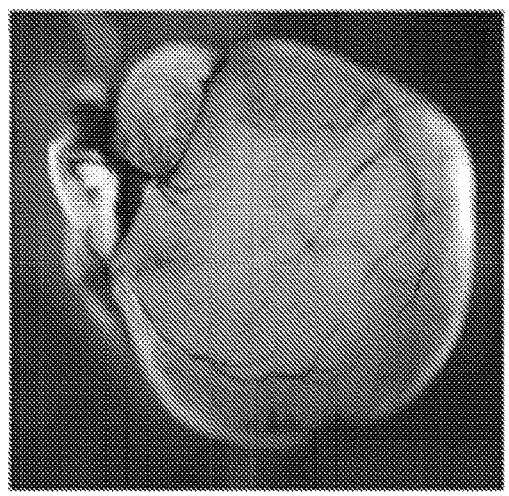
Figure 13A:
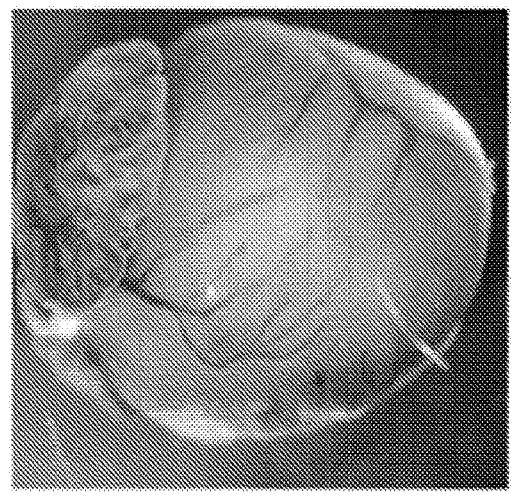
Figure 13B:
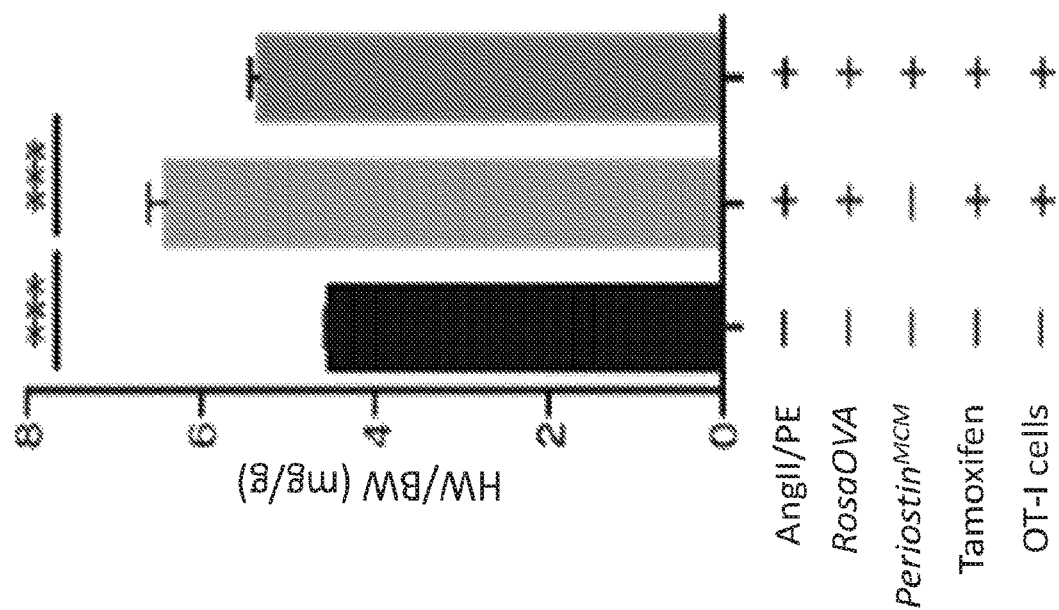

Mice were generated in which a xenogeneic antigen (ovalbumin peptide, OVA), not normally found in mice, could be conditionally presented on the surface of activated cardiac fibroblasts. To induce expression of OVA, a tamoxifen (Tam) inducible Cre recombinase targeted to the Periostin locus (Postn$^{MCM}$) was utilized. Postn has been shown to be expressed by activated cardiac fibroblasts induced by injury, but not by quiescent cardiac fibroblasts. In order to induce injury and fibrosis, OVA;Postn$^{MCM}$ mice were continuously infused with angiotensin II and phenylephrine (AngII/PE) for 28 days via osmotic minipump. Tamoxifen was administered at regular intervals by intraperitoneal injection to ensure near constant induction of Cre recombinase and expression of ovalbumin (FIG. 11A). AngII/PE administration has been widely demonstrated to induce dramatic cardiac fibrosis and dysfunction in mice by increasing afterload, chronotropy, and direct effects on cardiac myocytes and fibroblasts. Consistent with previous reports, significant and widespread fibrosis was observed throughout the myocardium of OVA;Postn$^{MCM}$ mice as early as one week following exposure to AngII/PE (FIG. 12). To selectively target OVA-expressing cells and their derivatives, adoptive transfer of CD8$^+$ cells that express a cognate T-cell receptor against the OVA peptide (CD8+ OT-I T cells) was performed in a cohort of mice one week after AngII/PE pump implantation after pathological fibrosis was established. Control animals included OVA+ mice lacking the Postn$^{MCM}$ allele that received AngII/PE, tamoxifen, and CD8+ OT-I cells (n>7 mice in each cohort). At week 4, widespread cardiac fibrosis was observed in the control animals. However, in marked contrast, significantly less cardiac fibrosis was observed in the OVA;Postn$^{MCM}$+Tam mice treated with OT-I T cells (FIG. 11B-11C). In addition to the reduced fibrosis, cardiac hypertrophy, as indicated by the heart-weight to body-weight ratio, was partially rescued after OT-I T cell adoptive transfer in OVA;Postn$^{MCM}$ mice (FIGS. 13A-13B).

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating heart disease and/or heart failure in a subject in need thereof, the method comprising administering to the subject a cell genetically modified to express a chimeric antigen receptor (CAR) or a T cell receptor (TCR), wherein the CAR or the TCR comprises an antigen binding domain that specifically binds fibroblast activation protein (FAP) on cardiac fibroblasts, wherein the antigen binding domain comprises six (6) CDRs of an amino acid sequence encoded by a nucleic acid sequence comprising SEQ ID NO: 2, thereby treating the heart disease and/or the heart failure.

2. The method of claim 1, wherein the heart disease is selected from the group consisting of cardiac fibrosis, hypertensive heart disease, diastolic dysfunction, heart failure with preserved ejection fraction, myocardial infarction, ischemic cardiomyopathy, hypertrophic cardiomyopathy, arrhythmia, atrial fibrillation, arrhythmogenic right ventricular dysplasia, dilated cardiomyopathy, an inherited form of heart disease, muscular dystrophy, infective cardiomyopathy, transplant cardiomyopathy, radiation induced cardiac fibrosis, an autoimmune related heart condition, sarcoid cardiomyopathy, lupus, a toxin related heart condition, a drug related heart condition, amyloidosis, diabetic cardiomyopathy, reactive interstitial fibrosis, replacement fibrosis, infiltrative interstitial fibrosis, and endomyocardial fibrosis.

3. The method of claim 1, wherein the cell is a T cell.

4. The method of claim 1, wherein the administering comprises adoptive cell transfer.

5. The method of claim 1, wherein the CAR comprises an amino acid sequence encoded by a nucleic acid sequence comprising SEQ ID NO: 1.

6. The method of claim 1, wherein the antigen binding domain comprises the amino acid sequence encoded by the nucleic acid sequence comprising SEQ ID NO: 2.

7. The method of claim 1, wherein the CAR is a switchable CAR.

8. The method of claim 7, further comprising administering a second agent to the subject to activate the switchable CAR.

9. The method of claim 1, wherein the heart disease is cardiac fibrosis.

10. The method of claim 1, wherein the administering comprises administering the cell genetically modified to express the CAR, and wherein the CAR further comprises an intracellular domain comprising a CD28 or 4-1BB signaling domain and a CD3-zeta signaling domain.

11. The method of claim 10, wherein the intracellular domain comprises the 4-1BB signaling domain and the CD3-zeta signaling domain, wherein the 4-1BB signaling domain comprises an amino acid sequence encoded by the nucleic acid sequence comprising SEQ ID NO: 4, and wherein the CD3-zeta signaling domain comprises an amino acid sequence encoded by the nucleic acid sequence comprising SEQ ID NO: 5.

* * * * *

UNITED STATES PATENT AND TRADEMARK OFFICE
CERTIFICATE OF CORRECTION

| | |
|---|---|
| PATENT NO. | : 11,786,551 B2 |
| APPLICATION NO. | : 16/651144 |
| DATED | : October 17, 2023 |
| INVENTOR(S) | : Jonathan Epstein et al. |

It is certified that error appears in the above-identified patent and that said Letters Patent is hereby corrected as shown below:

In the Specification

In Column 1, after the heading "STATEMENT REGARDING FEDERALLY SPONSORED RESEARCH OR DEVELOPMENT," please replace the paragraph at Lines 21-24 with the following paragraph:
--This invention was made with government support under HL140018, HL007843, and HL118768 awarded by the National Institutes of Health. The government has certain rights in the invention.--

Signed and Sealed this
Nineteenth Day of December, 2023

Katherine Kelly Vidal
*Director of the United States Patent and Trademark Office*

SEQUENCE LISTING

```
<160> NUMBER OF SEQ ID NOS: 5

<210> SEQ ID NO 1
<211> LENGTH: 1482
<212> TYPE: DNA
<213> ORGANISM: Artificial Sequence
<220> FEATURE:
<223> OTHER INFORMATION: FAP-CAR

<400> SEQUENCE: 1
atggccctgc ctgtgacagc cctgctgctg cctctggctc tgctgctgca tgccgctaga      60
cctggatccc aggtgcagct gaaagagtcc ggcggaggac tggtgcagcc tggcggatct     120
ctgaagctga gctgtgctgc cagcggcttc accttcagca gctacggcat gagctgggtg     180
cgacagaccg ccgacaagag actggaactg gtggctacca ccaacaacaa cggcggcgtg     240
acctactacc ccgacagcgt gaagggcaga ttcaccatct ccagagacaa cgccaagaac     300
accctgtacc tgcagatgag cagcctgcag agcgaggaca ccgccatgta ctactgcgcc     360
agatacggct actacgccat ggattactgg ggcagggca tcagcgtgac cgtgtctagc     420
ggaggcggcg gatctggcgg aggggatct agtggcggag gctctgacgt gctgatgacc     480
cagacacctc tgagcctgcc agtgtccctg ggcgaccagg ccagcatcag ctgtagaagc     540
agccagagca tcgtgcacag caacggcaac acctacctgg aatggtatct gcagaagccc     600
ggccagagcc ccaagctgct gatctacaag gtgtccaaca gattcagcgg cgtgcccgac     660
agattctccg gcagcggctc tggcaccgac ttcaccgtga agatctccag ggtggaagcc     720
gaggacctgg gcgtgtacta ctgttttcaa ggcagccacg tgccctacac cttcggcgga     780
ggcaccaagc tggaaatcaa ggctagctcc ggaaccacga cgccagcgcc gcgaccacca     840
acaccggcgc ccaccatcgc gtcgcagccc ctgtccctgc gcccagaggc gtgccggcca     900
gcggcggggg gcgcagtgca cacgagggg ctggacttcg cctgtgatat ctacatctgg     960
gcgcccttgg ccgggacttg tggggtcctt ctcctgtcac tggttatcac cctttactgc    1020
aaacggggca gaaagaaact cctgtatata ttcaaacaac catttatgag accagtacaa    1080
actactcaag aggaagatgg ctgtagctgc cgatttccag aagaagaaga aggaggatgt    1140
gaactgagag tgaagttcag caggagcgca gacgccccccg cgtacaagca gggccagaac    1200
```

| | |
|---|---|
| cagctctata acgagctcaa tctaggacga agagaggagt acgatgtttt ggacaagaga | 1260 |
| cgtggccggg accctgagat gggggggaaag ccgagaagga agaaccctca ggaaggcctg | 1320 |
| tacaatgaac tgcagaaaga taagatggcg gaggcctaca gtgagattgg gatgaaaggc | 1380 |
| gagcgccgga ggggcaaggg gcacgatggc ctttaccagg gtctcagtac agccaccaag | 1440 |
| gacacctacg acgcccttca catgcaggcc ctgccccctc gc | 1482 |

<210> SEQ ID NO 2
<211> LENGTH: 732
<212> TYPE: DNA
<213> ORGANISM: Artificial Sequence
<220> FEATURE:
<223> OTHER INFORMATION: Anti-mFAP scFv

<400> SEQUENCE: 2

| | |
|---|---|
| caggtgcagc tgaaagagtc cggcggagga ctggtgcagc ctggcggatc tctgaagctg | 60 |
| agctgtgctg ccagcggctt caccttcagc agctacggca tgagctgggt gcgacagacc | 120 |
| gccgacaaga gactggaact ggtggctacc accaacaaca acggcggcgt gacctactac | 180 |
| cccgacagcg tgaagggcag attcaccatc tccagagaca cgccaagaa caccctgtac | 240 |
| ctgcagatga gcagcctgca gagcgaggac accgccatgt actactgcgc cagatacggc | 300 |
| tactacgcca tggattactg gggccagggc atcagcgtga ccgtgtctag cggaggcggc | 360 |
| ggatctggcg gagggggatc tagtggcgga ggctctgacg tgctgatgac ccagacacct | 420 |
| ctgagcctgc cagtgtccct gggcgaccag gccagcatca gctgtagaag cagccagagc | 480 |
| atcgtgcaca gcaacggcaa cacctacctg aatggtatc tgcagaagcc cggccagagc | 540 |
| cccaagctgc tgatctacaa ggtgtccaac agattcagcg gcgtgcccga cagattctcc | 600 |
| ggcagcggct ctggcaccga cttcaccgtg aagatctcca gggtggaagc cgaggacctg | 660 |
| ggcgtgtact actgttttca aggcagccac gtgccctaca ccttcggcgg aggcaccaag | 720 |
| ctggaaatca ag | 732 |

<210> SEQ ID NO 3
<211> LENGTH: 72
<212> TYPE: DNA
<213> ORGANISM: Artificial Sequence
<220> FEATURE:
<223> OTHER INFORMATION: CD8a transmembrane domain

<400> SEQUENCE: 3

| | |
|---|---|
| atctacatct gggcgccctt ggccgggact tgtggggtcc ttctcctgtc actggttatc | 60 |
| acccttact gc | 72 |

<210> SEQ ID NO 4
<211> LENGTH: 126
<212> TYPE: DNA
<213> ORGANISM: Artificial Sequence
<220> FEATURE:
<223> OTHER INFORMATION: 4-1BB intracellular domain

<400> SEQUENCE: 4

| | |
|---|---|
| aaacggggca gaaagaaact cctgtatata ttcaaacaac catttatgag accagtacaa | 60 |
| actactcaag aggaagatgg ctgtagctgc cgatttccag aagaagaaga aggaggatgt | 120 |
| gaactg | 126 |

<210> SEQ ID NO 5

```
<211> LENGTH: 336
<212> TYPE: DNA
<213> ORGANISM: Artificial Sequence
<220> FEATURE:
<223> OTHER INFORMATION: CD3-zeta signaling domain

<400> SEQUENCE: 5
agagtgaagt tcagcaggag cgcagacgcc cccgcgtaca agcagggcca gaaccagctc        60
tataacgagc tcaatctagg acgaagagag gagtacgatg tttttggacaa gagacgtggc       120 cgggaccctg agatgggggg aaagccgaga aggaagaacc ctcaggaagg cctgtacaat       180
gaactgcaga aagataagat ggcggaggcc tacagtgaga ttgggatgaa aggcgagcgc       240
cggaggggca aggggcacga tggcctttac cagggtctca gtacagccac caaggacacc       300
tacgacgccc ttcacatgca ggccctgccc cctcgc                                  336
```